United States Patent
Laux et al.

[19]

[11] Patent Number: 5,904,675
[45] Date of Patent: May 18, 1999

[54] ABSORBENT ARTICLE WITH IMPROVED ELASTIC MARGINS AND CONTAINMENT SYSTEM

[75] Inventors: Daniel Richard Laux; Lynn Carol Brud, both of Appleton; Barbara Ann Gossen, Oshkosh; Eric Donald Johnson, Larsen; Cynthia Helen Nordness, Oshkosh; Deborah Lynn Proxmire, Larsen; Mark Louis Robinson, Appleton; Paula Mary Sosalla, Appleton; Robert Alan Stevens, Appleton, all of Wis.

[73] Assignee: Kimberly-Clark Worldwide, Inc., Neenah, Wis.

[21] Appl. No.: 08/950,105

[22] Filed: Oct. 16, 1997

Related U.S. Application Data

[63] Continuation of application No. 08/560,525, Dec. 18, 1995, abandoned.

[51] Int. Cl.$^6$ ...................................................... A61F 13/15
[52] U.S. Cl. ........................................ 604/385.2; 604/386
[58] Field of Search ................................. 604/385.1–387, 604/378, 391, 393

[56] References Cited

U.S. PATENT DOCUMENTS

| | | | |
|---|---|---|---|
| H1630 | 1/1997 | Roe et al. ............................ | 604/385.2 |
| 2,532,029 | 11/1950 | Medoff . | |
| 2,545,674 | 3/1951 | Ralph . | |
| 2,575,163 | 11/1951 | Donovan . | |
| 2,575,164 | 11/1951 | Donovan . | |
| 2,893,393 | 7/1959 | Pressley . | |
| 2,956,564 | 10/1960 | Ohara . | |
| 3,386,442 | 6/1968 | Sabee . | |
| 3,901,236 | 8/1975 | Assarsson et al. . | |
| 4,076,663 | 2/1978 | Masuda et al. . | |
| 4,286,082 | 8/1981 | Tsubakimoto et al. . | |
| 4,381,781 | 5/1983 | Sciaraffa et al. ........................ | 604/372 |
| 4,585,448 | 4/1986 | Enloe ..................................... | 604/378 |
| 4,636,207 | 1/1987 | Buell ..................................... | 604/370 |
| 4,657,539 | 4/1987 | Lasse . | |

(List continued on next page.)

FOREIGN PATENT DOCUMENTS

| | | |
|---|---|---|
| 0217032 A3 | 4/1987 | European Pat. Off. . |
| 0243013 A1 | 10/1987 | European Pat. Off. . |
| 0312071 A2 | 4/1989 | European Pat. Off. . |
| 0324133 B1 | 7/1989 | European Pat. Off. . |
| 0339461 B1 | 11/1989 | European Pat. Off. . |
| 0376022 B1 | 7/1990 | European Pat. Off. . |
| 0386815 A2 | 9/1990 | European Pat. Off. . |
| 0403832 B1 | 12/1990 | European Pat. Off. . |
| 0433951 A2 | 6/1991 | European Pat. Off. . |
| 0 532 035 A3 | 3/1993 | European Pat. Off. . |

(List continued on next page.)

OTHER PUBLICATIONS

Derwent World Patent Database abstract of FR 2,680,316: Description of B. Deleu et al., "Disposable Nappy.".

*Primary Examiner*—Mark O. Polutta
*Attorney, Agent, or Firm*—Paul Yee

[57] ABSTRACT

An absorbent article has a longitudinal length dimension, a lateral cross dimension, a front waistband portion, a back waistband portion and an intermediate portion which interconnects the front and back waistband portions. The article includes a backsheet layer having a pair of laterally opposed side margins, with each side margin having an outwardly concave, terminal side edge contour located at appointed leg opening regions in an intermediate portion of each of the side margins. Each concave side edge contour has a selected longitudinal extent along the length dimension of the article. A liquid permeable topsheet layer is connected in superposed relation to the backsheet layer, and an absorbent body is sandwiched between the topsheet layer and the backsheet layer. A separate, elasticized and gathered leg gusset is connected to the article along each of the appointed leg opening regions, and each leg gusset is configured to extend beyond and to bridge between opposed, spaced-apart portions of an associated one of the concave side edge contours of the backsheet layer.

18 Claims, 10 Drawing Sheets

U.S. PATENT DOCUMENTS

| | | | |
|---|---|---|---|
| 4,662,877 | 5/1987 | Williams . | |
| 4,663,220 | 5/1987 | Wisneski et al. | 428/221 |
| 4,695,278 | 9/1987 | Lawson . | |
| 4,699,823 | 10/1987 | Kellenberger et al. | 428/219 |
| 4,704,116 | 11/1987 | Enloe . | |
| 4,738,677 | 4/1988 | Foreman . | |
| 4,743,246 | 5/1988 | Lawson . | |
| 4,753,646 | 6/1988 | Enloe . | |
| 4,770,656 | 9/1988 | Proxmire et al. | 604/393 |
| 4,795,454 | 1/1989 | Dragoo | 604/385.2 |
| 4,816,025 | 3/1989 | Foreman | 604/385.2 |
| 4,822,435 | 4/1989 | Igaue et al. . | |
| 4,834,740 | 5/1989 | Suzuki et al. | 604/385.2 |
| 4,846,823 | 7/1989 | Enloe | 604/385.2 |
| 4,846,825 | 7/1989 | Enloe et al. | 604/385.1 |
| 4,861,652 | 8/1989 | Lippert et al. . | |
| 4,883,480 | 11/1989 | Huffman et al. | 604/385.1 |
| 4,892,528 | 1/1990 | Suzuki et al. | 604/385.2 |
| 4,904,251 | 2/1990 | Igaue et al. | 604/385.2 |
| 4,916,005 | 4/1990 | Lippert et al. | 428/192 |
| 4,938,754 | 7/1990 | Mesek | 604/385.2 |
| 4,938,755 | 7/1990 | Foreman | 604/385.2 |
| 4,998,929 | 3/1991 | Björksund et al. | 604/385.2 |
| 5,019,066 | 5/1991 | Freeland et al. | 604/385.2 |
| 5,026,364 | 6/1991 | Robertson | 604/385.1 |
| 5,028,224 | 7/1991 | Pieper et al. | 425/80.1 |
| 5,032,120 | 7/1991 | Freeland et al. | 604/385.2 |
| 5,061,261 | 10/1991 | Suzuki et al. | 604/385.2 |
| 5,064,489 | 11/1991 | Ujimoto et al. | 156/164 |
| 5,080,658 | 1/1992 | Igaue et al. | 604/385.2 |
| 5,085,654 | 2/1992 | Buell | 604/370 |
| 5,114,420 | 5/1992 | Igaue et al. | 604/385.2 |
| 5,137,526 | 8/1992 | Coates | 604/391 |
| 5,147,343 | 9/1992 | Kellenberger | 604/368 |
| 5,167,653 | 12/1992 | Igaue et al. | 604/385.2 |
| 5,176,672 | 1/1993 | Bruemmer et al. | 604/385.1 |
| 5,221,277 | 6/1993 | Beplate | 604/394 |
| 5,226,992 | 7/1993 | Morman | 156/62.4 |
| 5,246,432 | 9/1993 | Suzuki et al. | 604/385.2 |
| 5,275,590 | 1/1994 | Huffman et al. | 604/385.2 |
| 5,292,316 | 3/1994 | Suzuki | 604/385.2 |
| 5,304,159 | 4/1994 | Tanji et al. | 604/385.2 |
| 5,304,160 | 4/1994 | Igaue et al. | 604/385.2 |
| 5,330,598 | 7/1994 | Erdman et al. | 156/164 |
| 5,342,342 | 8/1994 | Kitaoka | 604/385.2 |
| 5,344,516 | 9/1994 | Tanji et al. | 156/164 |
| 5,360,422 | 11/1994 | Brownlee et al. | 604/385.2 |
| 5,368,584 | 11/1994 | Clear et al. | 604/385.2 |
| 5,397,318 | 3/1995 | Dreier | 604/385.2 |
| 5,399,219 | 3/1995 | Roessler et al. | 156/259 |
| 5,409,476 | 4/1995 | Coates | 604/391 |
| 5,451,219 | 9/1995 | Suzuki et al. | 604/385.2 |
| 5,489,282 | 2/1996 | Zehner et al. | 604/385.1 |
| 5,562,650 | 10/1996 | Everett et al. | 604/378 |
| 5,569,227 | 10/1996 | Vandemoortele et al. | 604/382 |
| 5,576,091 | 11/1996 | Zajackaski et al. | 604/385.2 |

FOREIGN PATENT DOCUMENTS

| | | |
|---|---|---|
| 0329160 B1 | 9/1993 | European Pat. Off. . |
| 0 568 085 A1 | 11/1993 | European Pat. Off. . |
| 0 622 063 A3 | 11/1994 | European Pat. Off. . |
| 0 678 289 A1 | 10/1995 | European Pat. Off. . |
| 2677541 A1 | 12/1992 | France . |
| 2 680 316 A1 | 2/1993 | France . |
| 7-184954 | 7/1995 | Japan . |
| 7-184955 | 7/1995 | Japan . |
| 92/4165 | 6/1992 | South Africa . |
| 2159693 | 12/1985 | United Kingdom . |
| 2216393 | 10/1989 | United Kingdom . |
| 2262873 | 7/1993 | United Kingdom . |
| 2265550 | 10/1993 | United Kingdom . |
| 2265834 | 10/1993 | United Kingdom . |
| 2266055 | 10/1993 | United Kingdom . |
| 2266225 | 10/1993 | United Kingdom . |
| 2266444 | 11/1993 | United Kingdom . |
| 2268389 | 1/1994 | United Kingdom . |
| 2270247 | 3/1994 | United Kingdom . |
| 2275610 | 9/1994 | United Kingdom . |
| 2275611 | 9/1994 | United Kingdom . |
| 2278993 | 12/1994 | United Kingdom . |
| 2280374 | 2/1995 | United Kingdom . |
| 2285409 | 7/1995 | United Kingdom . |
| 9108717 | 6/1991 | WIPO . |
| 9207533 | 5/1992 | WIPO . |
| 9209253 | 6/1992 | WIPO . |
| 9212648 | 8/1992 | WIPO . |
| 9305742 | 4/1993 | WIPO . |
| 9312746 | 7/1993 | WIPO . |
| 9323000 | 11/1993 | WIPO . |
| 9418927 | 9/1994 | WIPO . |
| WO 94/18927 A1 | 9/1994 | WIPO . |
| 9514453 | 6/1995 | WIPO . |
| 9522951 | 8/1995 | WIPO . |
| WO 96/05792 A1 | 2/1996 | WIPO . |
| WO 96/31176 | 10/1996 | WIPO . |

5,904,675

ABSORBENT ARTICLE WITH IMPROVED ELASTIC MARGINS AND CONTAINMENT SYSTEM

This application is a continuation of application Ser. No. 08/560,525 entitled "AN ABSORBENT ARTICLE WITH IMPROVED ELASTIC MARGINS AND CONTAINMENT SYSTEM" and filed in the U.S. Patent and Trademark Office on Dec. 18, 1995, now abandoned. The entirety of this application is hereby incorporated by reference.

FIELD OF THE INVENTION

The present invention relates to an article having one or more elasticized, peripheral margins. More particularly, the invention relates to an article which incorporates a distinctively elasticized containment system at legband and/or waistband portions of the article.

BACKGROUND OF THE INVENTION

Conventional absorbent articles, such as disposable diapers, have been constructed with various types of elasticized waistbands and elasticized leg bands or leg cuffs. Such article have also included additional, elasticized containment or barrier flaps at the leg and/or waist sections of the article. Particular article designs have incorporated a stretchable outer cover composed of an elastomeric web material, such as a stretch-bonded laminate which includes a layer of nonwoven fabric. Other conventional designs have included separate elastomeric or nonelastomeric side panel members connected to the lateral side edges of a backsheet or outercover member, and have included fastening systems and fastening tabs connected to the side panels for securing the article on a wearer.

Articles which incorporate conventional barrier flap configurations at their legband and waist sections, however, have exhibited various shortcomings. For example, it has been difficult to maintain the desired operation of the barrier flaps when the articles are being worn. Even when the barrier flaps are constructed of an elastomeric material or otherwise elasticized, it has been difficult to maintain contact between the movable edge of the barrier flap and the wearer's body and has been difficult to reliably hold the flap open for an effective receipt and containment of urine and feces. As a result, there has been a continued need for improved containment structures at the leg and waist regions of the absorbent articles.

BRIEF DESCRIPTION OF THE INVENTION

The present invention can provide a distinctive article having a longitudinal length dimension, a lateral cross dimension, a front waistband portion, a back waistband portion and an intermediate portion which interconnects the front and back waistband portions. The article includes a backsheet layer having a pair of laterally opposed side margins, with each side margin having a terminal side edge contour, such as an outwardly concave terminal side edge contour, located at appointed leg opening regions in each of the side margins. Each side edge contour has a selected longitudinal extent along the length dimension of the article. A liquid permeable topsheet layer is connected in superposed relation to the backsheet layer, and an absorbent body is sandwiched between the topsheet layer and the backsheet layer. A separate, elasticized leg gusset is connected to the article along each of the appointed leg opening regions, and each leg gusset is configured to extend beyond and to bridge between opposed, spaced-apart portions of an associated one of the side edge contours of the backsheet layer.

In particular aspects, the invention can include a pair of elasticized, laterally opposed and longitudinally extending containment flaps which are connected to at least one of the backsheet and topsheet layers. Each containment flap can have a movable edge portion, and a fixed edge located proximally adjacent to a one of the elasticized leg openings, each containment flap can also include a substantially liquid impermeable barrier layer and a nonwoven fabric layer connected in facing relation with the barrier layer. In addition, a plurality of separate, longitudinally extending elastomeric members are sandwiched between the barrier layer and the fabric layer to provide an elasticized composite which is substantially longitudinally gathered. Each containment flap includes at least one of the elastomeric members attached to the containment flap at a location which is proximate the movable edge of the containment flap.

In yet other aspects, the invention can include a separate gusset-flap member which is connected to at least one of the backsheet and topsheet layers along each of the appointed leg opening regions, and which includes a leg gusset section and a containment flap section. Each leg gusset section is configured to extend beyond and bridge across its associated side edge contour of the backsheet layer, and each leg gusset section provides an elasticized and gathered outboard side margin of the article. Each containment flap section is integrally formed with a one of the leg gusset sections to provide a gusset-flap composite. Each containment flap section has a substantially fixed edge located proximally adjacent to a one of the elasticized side margins, and has an elasticized and gathered, distal, movable edge portion. Each gusset-flap member includes a substantially liquid impermeable barrier layer, and a nonwoven fabric layer which is substantially coextensive with the barrier layer, and is connected in a superposed, facing relation with the barrier layer. A plurality of longitudinally extending elastomeric members are sandwiched between the gusset-flap barrier layer and the gusset-flap fabric layer to provide an elasticized gusset-flap composite which is substantially longitudinally gathered.

The various aspects of the invention can provide a barrier flap structure that can more reliably and more effectively maintain an open position when the associated absorbent article is being worn. In addition, the open flap configuration can be sustained while avoiding excessive irritation of the wearer's skin. The arrangements of the constituent components and the combination of operational parameters, such as the controlled stiffness and the controlled articulation of the barrier flap, can advantageously provide an improved absorbent structure which can have less leakage, and can afford increased comfort to the wearer.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The present invention will be described herein in relationship to producing an elasticized containment system for absorbent articles, particularly disposable absorbent articles. The articles can be placed against or in proximity to the body of a wearer to absorb and contain various exudates discharged from the body, and are intended to be discarded after a limited period of use. The articles are not intended to be laundered or otherwise restored for re-use. While the present description will particularly be made in the context of a diaper article, it should be understood that the present invention is also applicable to other articles, such as caps, gowns, drapes, covers, adult incontinence garments, sanitary napkins, children's training pants, and the like.

In addition, the invention will be described in the context of its various configurations and aspects. It should be appreciated that alternative arrangements of the invention can comprise any combination which includes one or more of the various configurations and aspects of the invention.

Figure 1:
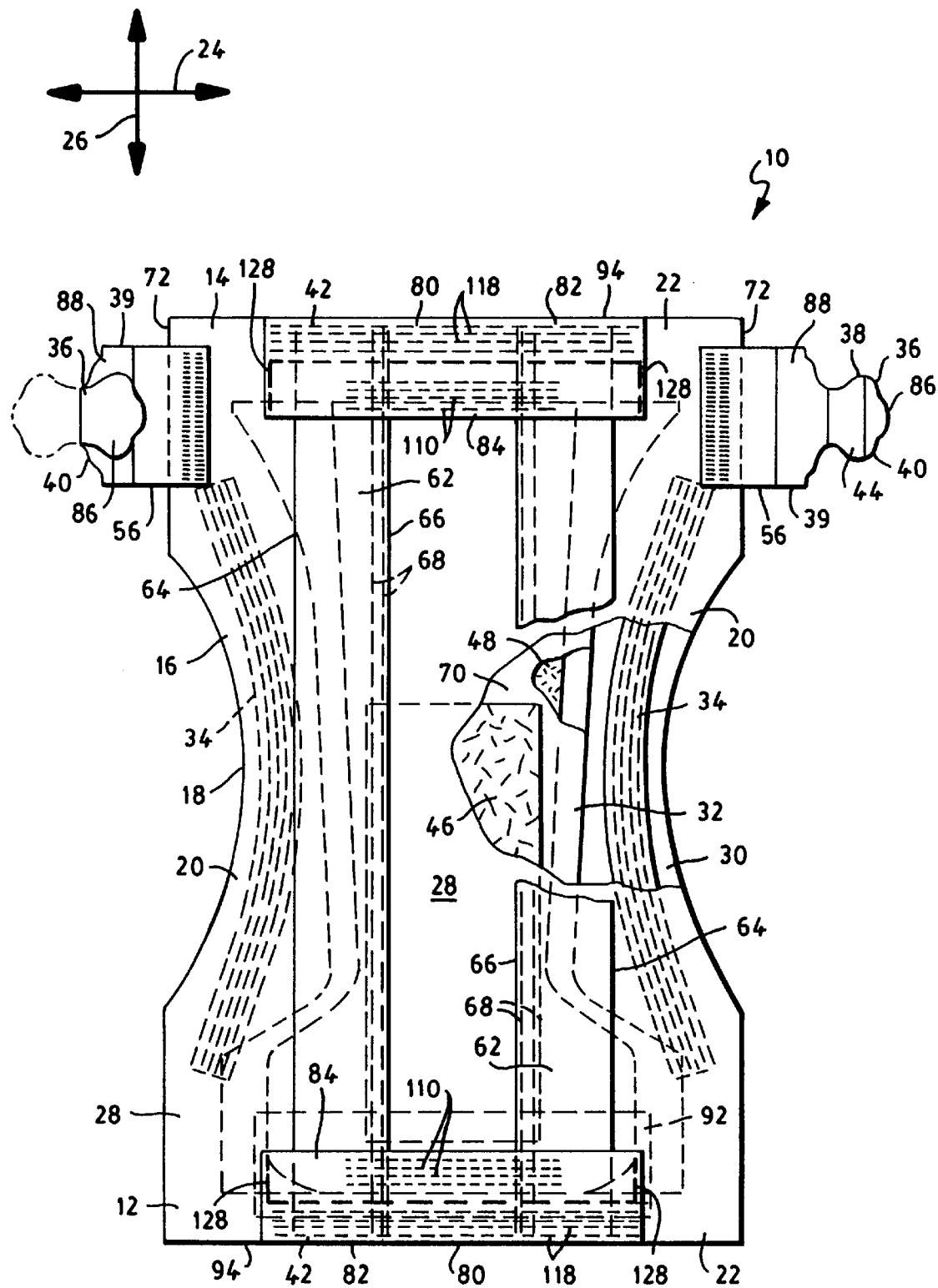
FIG. 1 representatively shows a partially cut-away, top view of an article of the invention.
Figure 2:
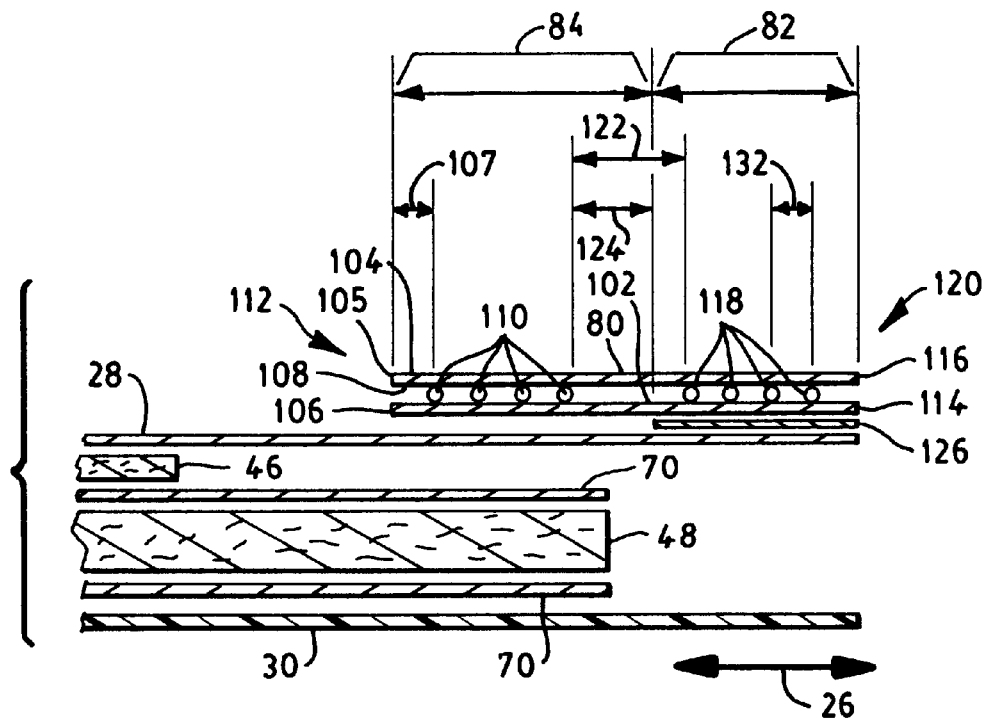
FIG. 2 representatively shows a schematic, expanded cross-sectional view of the waist elastic system and the waist, barrier flap system of the invention taken along a longitudinal centerline of the article when the flap or pocket section is in its flat-out, uncontracted condition.
Figure 3:
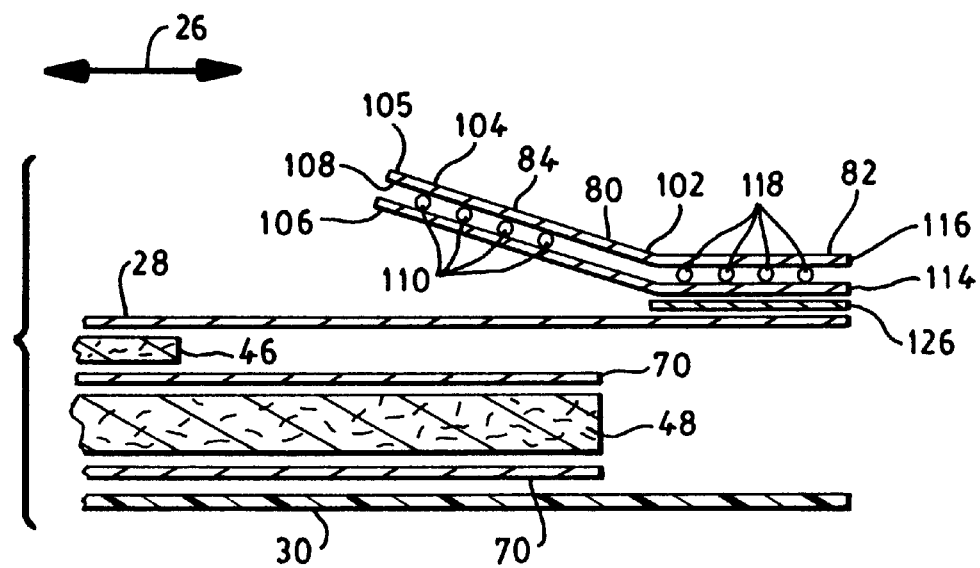
FIG. 3 representatively shows a schematic, expanded cross-sectional view of the waist elastic system and the waist, barrier flap system of the invention taken when the flap or pocket section is in its contracted and opened condition.

With reference to FIGS. 1, 2 and 3, a representative article, such as a diaper 10, includes a longitudinal length dimension 26, a lateral cross-dimension 24, a front waistband portion 12, a back waistband portion 14, an intermediate portion 16 which interconnects the front and back waistband portions, and a pair of laterally opposed elasticized side margins 20. The article has a backsheet layer 30, and a liquid permeable topsheet layer 28 connected in superposed relation to the backsheet layer. An absorbent body structure 32 is sandwiched between the topsheet layer and the backsheet layer, and an elasticized, waist pocket member 80 can be connected to at least one of the backsheet and topsheet layers along at least one end margin 22 of the article.

The representatively shown article includes longitudinally opposed end margins 22 and a pair of laterally opposed elasticized side margins 20. The elasticized, waist pocket member 80 is connected to at least one of the backsheet and topsheet layers along at least one end margin 22 of the article. The shown waist pocket member 80 includes an extending flange section 82 and an extending pocket section 84. The pocket section 84 of the waist pocket member 80 includes a substantially fixed edge portion 102 secured to the article, and includes an elasticized, gathered moveable edge portion 104 which is longitudinally spaced from the fixed edge portion 102. The pocket section also includes a substantially liquid impermeable pocket barrier layer 106, and a pocket fabric layer 108 connected in facing relation with the pocket barrier layer. A plurality of separate, laterally extending pocket elastic members 110 are sandwiched between the pocket barrier layer 106 and the pocket fabric layer 108 to provide an elasticized waist pocket composite 112 which is substantially laterally gathered.

A fastening system 40 is connected to the article at either or both of the laterally opposed end regions 72 of at least one of the front and rear waistband sections. A cooperating side panel member 56 can be associated with each fastening system and may be constructed to be nonelasticized, or to be elastically stretchable at least along a laterally extending cross-direction 24 of the article.

Figure 7:
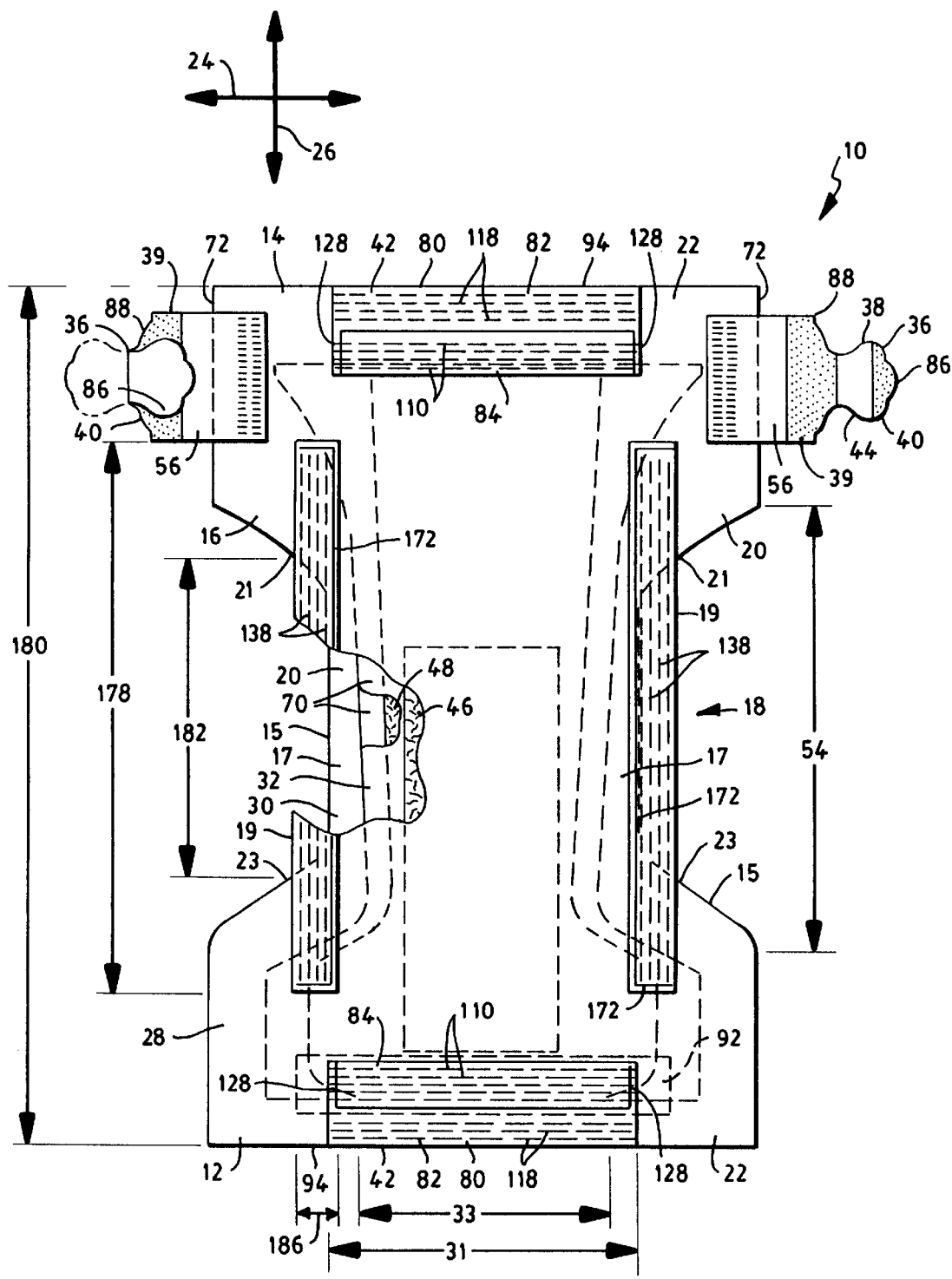
FIG. 7 representatively shows a partially cut-away, top view of another article of the invention having a laterally opposed pair of leg gusset members.
Figure 8:
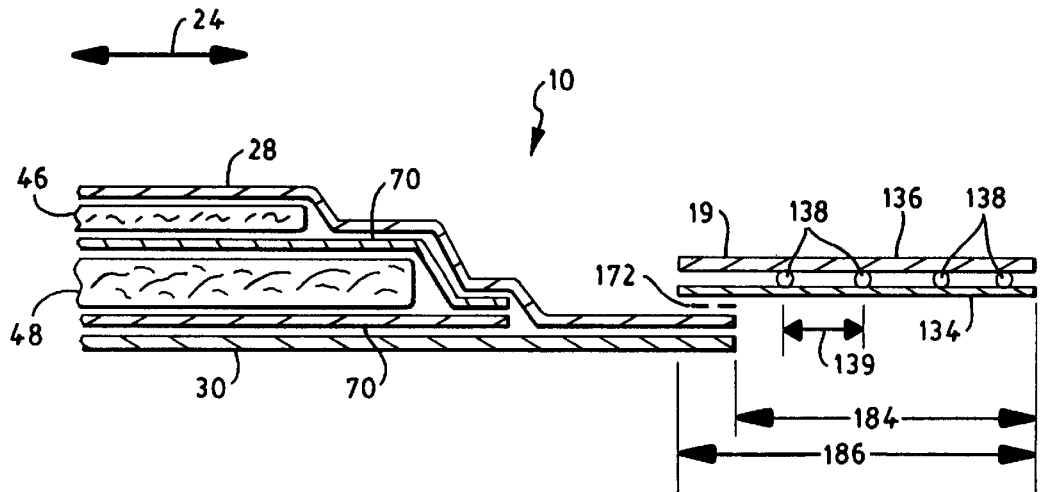
FIG. 8 a schematic, expanded, lateral cross-sectional view of one of the leg gusset members taken through the crotch section of the article.

With reference to FIGS. 7 and 8, an article, such as diaper 10, has a cross-wise, lateral dimension 24, a length-wise, longitudinal dimension 26, laterally opposed side margins and longitudinally opposed end margins. The representative diaper 10, provides a front waistband portion 12, a rear or back waistband portion 14, and an intermediate portion 16 which interconnects the front and rear waistband portions. The article includes a backsheet layer 30 having a laterally extending width and a longitudinally extending length. The backsheet layer also has a pair of laterally opposed side margins 20, with each side margin having a selected side edge contour, such as the shown outwardly concave, terminal side edge contour 15, located at appointed leg opening or legband regions 17 in an intermediate portion of each of the side margins. Each concave side edge contour 15 has a selected longitudinal extent 54 along the length dimension of the article. A porous, liquid permeable topsheet layer 28 has a laterally extending width and a longitudinally extending length, and is connected in superposed relation to the backsheet layer 30. An absorbent body structure 32, is sandwiched and operably secured between the backsheet layer 30 and the topsheet layer 28. A separate, elasticized and gathered leg gusset 19 is connected to the article along each of the appointed leg opening regions 17, and each leg gusset 19 is configured to extend beyond and past the concave side edge contours 15 of the backsheet layer 30 to provide an elasticized leg cuff in at least the intermediate portion of the article. Additionally, each leg gusset 19 is configured to bridge between opposed, spaced-apart portions 21 and 23 of an associated one of the concave side edge contours 15 of the backsheet layer 30. In particular arrangements, each leg gusset member 19 is operably attached to the inward, bodyside surface of the topsheet 28, and alternatively, may be operably attached to an outward surface of the backsheet layer 30. Optionally, the leg gusset member may be operably attached to an inward surface of the backsheet layer, or sandwiched between the topsheet layer 28 and the backsheet layer 30.

Further aspects of the invention can provide an absorbent article in which the backsheet layer 30 may include a crotch region thereof having a crotch width 31 which is particularly narrow. Desirably the crotch width of the backsheet layer can be not more than about 11.5 cm. Other aspects of the invention can provide an article in which the absorbent body 32 is constructed with a crotch width thereof which is also quite narrow. Desirably the crotch region of the absorbent body can have a crotch width 33 which can be not more than about 7.6 cm, and in addition, the crotch width of the absorbent body can be at least about 55 percent (%) of the crotch width 31 of the backsheet layer 30. In still other aspects of the invention, each separate, elasticized and gathered leg gusset 19 can be connected to at least one of the topsheet and backsheet layers with a gusset attachment 172 which extends along each of the appointed leg opening regions. Each gusset attachment 172 can be spaced from an associated, proximally adjacent, longitudinally extending side edge of the absorbent body 32 by a distance of not more than about 1.3 cm, at least when measured within the crotch region 18 of the article. Each leg gusset is configured to extend beyond and to bridge between opposed spaced-apart portions 21 and 23 of an associated one of the concave side edge contours of the backsheet layer. The various aspects and configurations of the invention can provide distinctive combinations of softness, body conformity, reduced bunching between the wearer's legs, reduced red-marking of the wearer's skin, and improved leakage protection.

FIG. 1 is a representative plan view of diaper 10 of the present invention in its flat-out, uncontracted state (i.e., with all elastic induced gathering and contraction removed). Portions of the structure are partially cut away to more clearly show the interior construction of diaper 10, and the surface of the diaper which contacts the wearer is facing the viewer. The outer edges of the diaper define a periphery in which the longitudinally extending side edge margins are designated 20 and the laterally extending end edge margins are designated 22. The side edges define leg openings for the diaper, and optionally, are curvilinear and contoured. The end edges are shown as straight, but optionally, may be curvilinear.

Diaper 10 typically includes a porous, liquid permeable topsheet 28; a substantially liquid impermeable backsheet 30; an absorbent structure 32, positioned and connected between the topsheet and backsheet; a surge management portion 46; and elastic members, such as leg elastics 34 and waist elastics 42. The surge management portion is positioned in liquid communication with the absorbent structure, and the absorbent structure includes a retention portion 48. The topsheet 28, backsheet 30, absorbent structure 32, surge management portion 46 and the elastic members 34 and 42 may be assembled in a variety of well-known diaper configurations. In addition, the diaper can include a system of legband barrier flaps, such as containment flaps 62.

As representatively shown, the topsheet 28 and backsheet 30 may be generally coextensive, and may have length and width dimensions which are generally larger than the corresponding dimensions of absorbent structure 32. Topsheet 28 is associated with and superimposed on backsheet 30, thereby defining the periphery of diaper 10. The waistband regions comprise those upper portions of diaper 10, which when worn, wholly or partially cover or encircle the waist or mid-lower torso of the wearer. The intermediate, region 16 lies between and interconnects waistband regions 12 and 14, and includes a crotch region 18 which comprises that portion of diaper 10 which, when worn, is positioned between the legs of the wearer and covers the lower torso of the wearer. Thus, the crotch region 18 is an area where repeated fluid surges typically occur in the diaper or other disposable absorbent article.

Topsheet 28 presents a body-facing surface which is compliant, soft-feeling, and non-irritating to the wearer's skin. Further, the topsheet 28 can be less hydrophilic than retention portion 48, and is sufficiently porous to be liquid permeable, permitting liquid to penetrate through its thickness. A suitable topsheet 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 28 is typically employed to help isolate the wearer's skin from liquids held in absorbent structure 32. Various woven and nonwoven fabrics can be used for topsheet 28. For example, the topsheet may be composed of a meltblown or spunbonded web of polyolefin fibers. The topsheet may also be a bonded-carded-web composed of natural and/or synthetic fibers.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic and substantially nonwettable material, and the hydrophobic material may optionally be treated with a surfactant or otherwise processed to impart a desired level of wettability and hydrophilicity. In a particular embodiment of the invention, topsheet 28 can be a nonwoven, spunbond polypropylene fabric composed of about 2.8–3.2 denier fibers formed into a web having a basis weight of about 20 gsm (g/m$^2$) and density of about 0.13 gm/cc. The fabric can be surface treated with a selected amount of surfactant, such as about 0.28% TRITON X-102 surfactant available from Union Carbide, a business having offices in Danbury, Conn. The surfactant can be applied by any conventional means, such as spraying, printing, brush coating or the like.

The surfactant material, such as a conventional wetting agent, can be applied to a medial section of the topsheet layer 28 to provide a greater wettability of the medial section, as compared to a remainder of the topsheet layer 28. In particular configurations, the cross-directional width of the medial section can be substantially equal to or less than the cross-directional width of the surge management portion 46. In alternative configurations, the medial section width can be substantially equal to or less than a cross-directional spacing between a pair of adhesive strips employed to secure the containment flaps 62 onto topsheet 28 and to form a leak resistant barrier seal onto the backsheet 30.

The surfactant-treated medial section can be approximately centered with respect to the longitudinal centerline of the diaper, and can extend along substantially the entire length of the topsheet layer. Alternatively, the surfactant treated medial section can be constructed to extend along only a predetermined portion of the topsheet length.

The various configurations of the invention can include elasticized, legband barrier flaps, such as the illustrated containment flaps 62. The shown configurations, for example, include two containment flaps 62 which are connected to the bodyside surface of topsheet layer 28. Suitable constructions and arrangements for containment flaps 62 are described, for example, in U.S. Pat. No. 4,704,116 issued Nov. 3, 1987, to K. Enloe, the disclosure of which is hereby incorporated by reference in a manner that is consistent (not contradictory) herewith. Other configurations of the containment flaps 62 are described in U.S. patent application Ser. No. 206,816 of R. Everett et al., filed Mar. 4, 1994 and entitled ABSORBENT ARTICLE HAVING AN IMPROVED SURGE MANAGEMENT (Attorney docket No. 11,375),now U.S. Pat. No. 5,562,650, the disclosure of which is hereby incorporated by reference in a manner that is consistent herewith.

Such containment flaps can be attached to topsheet layer 28 along length-wise extending fixed regions, such as fixed edges 64, of the flaps. A movable edge 66 of each containment flap includes a flap elastic member 68 which can comprise one or more individual strands of elastomeric material. For example, a plurality of elastic strands may be configured in a spatially separated, generally parallel arrangement, and a suitable elastic strand can, for example, be composed of a 470 decitex LYCRA elastomer which is available from E. I. DuPont de Nemours, a business having offices in Wilmington, Del. Alternatively, the elastic strands may be composed of 700 denier GLOSPAN S7 spandex elastomer which is available from Globe Manufacturing, a business having offices in Fall River, Mass. Elastic member 68 is connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of topsheet 28 and/or surge management portion 46 toward a generally upright and approximately perpendicular configuration, especially in the crotch section of the diaper. In the shown embodiment, for example, the moveable edge of the containment flap is connected to the flap elastics by partially doubling the flap material back upon itself by a limited amount which is sufficient to enclose the flap elastics 68.

At least a pair of containment, barrier flaps 62 are connected to laterally opposed, longitudinally extending regions of topsheet layer 28, and the connected topsheet regions are located generally adjacent to laterally opposed side edge regions of the medial section of topsheet layer 28. The connected topsheet regions are located substantially laterally inboard of the leg elastics of the diaper article 10, but may optionally be located outboard of the leg elastics.

In the various configurations of the invention, the desired barrier flaps, such as the containment flaps 62 and the waist flaps 84, may, for example, be constructed of a fibrous material which is similar to the material comprising topsheet 28, or similar to the material comprising surge management portion 46. Other conventional materials, such as polymer films, may also be employed. In other aspects of the invention, the barrier flaps are constructed of a material which is permeable only to gas, such as ambient air. Alternative configurations of the invention can include barrier flaps which are constructed of a material which is resistant to a passage of aqueous liquid, such as urine, therethrough. For example, the barrier flaps may be constructed of a spunbond-meltblown-spunbond (SMS) laminate material. In the illustrated embodiment, for example, the barrier flaps can be constructed of a SMS material having a basis weight of about 0.75 oz/yd$^2$ (about 25 g/m$^2$). The spunbond layers are composed of polypropylene fibers, and the meltblown layer is composed of meltblown polypropylene fibers.

In the various configurations of the invention where selected materials or components, such as the barrier flaps 62 and/or 84, are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated Dec. 31, 1968.

Backsheet 30 may be composed of a liquid permeable material, but preferably comprises a material which is configured to be substantially impermeable to liquids. For example, a typical backsheet can be manufactured from a thin plastic film, or other flexible liquid-impermeable material. Such "flexible" materials are compliant and will readily conform to the general shape and contours of the wearer's body. Backsheet 30 can help prevent the exudates contained in absorbent structure 32 from wetting articles such as bedsheets and overgarments which contact diaper 10.

In particular embodiments of the invention, backsheet 30 is a polyethylene film having a thickness of from about 0.012 millimeters (0.5 mil) to about 0.051 millimeters (2.0 mil). In the shown embodiment, for example, the backsheet is a film having a thickness of about 0.032 mm (about 1.25 mil). Alternative constructions of the backsheet may comprise a woven or non-woven fibrous web layer which has been totally or partially constructed or treated to impart a desired level of liquid impermeability to selected regions of the backsheet that are adjacent or proximate the absorbent body. For example, a clothlike backsheet may be composed of an approximately 0.5 oz/yd$^2$ (about 17 g/m$^2$) basis weight, polypropylene spunbond fabric which is laminated and thermally bonded to a stretch-thinned polypropylene film having a thickness of about 0.0006 in (about 0.015 mm) and a film basis weight of about 14.5 g/m$^2$. Backsheet 30 typically provides the outer cover of the article. Optionally, however, the article may comprise a separate outer cover member which is in addition to the backsheet.

Backsheet 30 may optionally include a micro-porous, "breathable" material which permits vapors to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minn. The backsheet can also be embossed or otherwise provided with a matte finish to exhibit a more aesthetically pleasing appearance.

The size of backsheet 30 is typically determined by the size of absorbent structure 32 and the exact diaper design selected. Backsheet 30, for example, may have a generally T-shape, a generally I-shape or a modified hourglass shape, and may extend beyond the terminal edges of absorbent structure 32 by a selected distance, such as a distance within the range of about 1.3 centimeters to 2.5 centimeters (about 0.5 to 1.0 inch), to provide side margins.

Topsheet 28 and backsheet 30 are connected or otherwise associated together in an operable manner. As used therein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in selected regions, such as in areas along the diaper periphery, by attachment means (not shown), such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet 28 to backsheet 30. It should be readily appreciated that the above-described attachment means may also be employed to interconnect and assemble together the various other component parts of the article described herein.

In the representatively shown embodiment of the invention, the topsheet layer 28 is disposed and secured in facing relation with the backsheet layer 30 to retain and hold the retention portion 48 and the surge management 46 between the backsheet layer and the topsheet layer. The marginal side regions of topsheet layer 28 are operably connected to corresponding marginal side regions of the backsheet layer 30. Each of the attached marginal side regions of the topsheet and backsheet layers is located laterally outboard of its corresponding, associated side edge region of the surge management portion 46. In particular configurations of the invention, the topsheet 28 can include attached marginal end regions, which are located longitudinally outboard of the end edge regions of the retention portion 48 and/or surge management portion 46. Similarly, the backsheet 30 can include attached marginal end regions, which can be located longitudinally outboard of the end edge regions of the retention portion and/or surge management portion.

Elastic members 34 are disposed adjacent the periphery of diaper 10 along each of the longitudinal side edges 20. The leg elastic members 34 can be connected to either or both of the topsheet and backsheet layers to provide elasticized side margins of the diaper article, and can be arranged to draw and hold diaper 10 against the legs of the wearer to provide elasticized leg bands or leg cuffs. Waist elastic members 42 may also be disposed adjacent either or both of the end edges of diaper 10 to provide elasticized waistbands.

Elastic members 34 and 42 are secured to diaper 10 in an elastically contractible condition so that in a normal under strain configuration, the elastic members effectively contract against diaper 10. The elastic members can be secured in an elastically contractible condition in a number of ways; for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other means, such as heat-shrink elastic material, may be used to gather the garment.

In the embodiment illustrated in FIG. 1, leg elastic members 34 extend essentially along the complete length of intermediate region 16 of diaper 10. Alternatively, elastic members 34 may extend the entire length of diaper 10, or any other length suitable providing the arrangement of elastically contractible lines desired for the particular diaper design. Elastic members 34 and 42 may have any of a variety of configurations. For example, the width of the individual elastic members 34 may be varied from 0.25 millimeters (0.01 inches) to 25 millimeters (1.0 inches) or more. The elastic members may comprise a single strand of elastic material, or may comprise several parallel or non-parallel strands of elastic material, and the elastic members may be applied in a rectilinear or curvilinear arrangement. Where multiple strands are employed, the individual strands may be constructed to provide substantially equal elastic forces, or may be constructed to provide different elastic forces. For example, the individual strands may be of different diameter or other size, or may be configured with different amounts of elongation to thereby provide a gradient or other variation of elastic tensions. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with selected patterns of hotmelt or other type of adhesive. For example, sprayed or swirled adhesive patterns may be employed.

In particular embodiments of the invention, for example, leg elastic members 34 may comprise a carrier sheet to which are attached a grouped set of elastics composed of a plurality of individual elastic strands. The elastic strands may intersect or be interconnected, or be entirely separated from one another. The shown carrier sheet may, for example, comprise a 0.002 cm thick film of unembossed polypropylene material. The shown elastic strands can, for example, be composed of LYCRA elastomer which is available from DuPont. Each elastic strand is typically within the range of about 620–1050 decitex (dtx), and preferably, is about 940 dtx in an embodiment of the invention wherein three strands are employed for each elasticized legband. In addition, leg elastics 34 may be generally straight or optionally curved. For example, the curved elastics can be inwardly bowed toward the longitudinal centerline of the diaper. In particular arrangements, the curvature of the elastics may or may not be configured or positioned symmetrically relative to the lateral centerline of the diaper. The curved elastics may have an inwardly bowed and outwardly bowed, reflex-type of curvature, and the length-wise center of the elastics may be offset by a selected distance toward either the front or rear waistband of the diaper to provide desired fit and appearance.

Conventional articles have incorporated various barrier flap structures at their waistband and/or legband regions. For example, such articles have typically incorporated a single or multi-layer piece of material, such as polymer films and film-nonwoven laminates, at the waistband portion of the article along the lateral cross-direction to form a waist flap or dam. The materials, however, typically exhibit similar behavior. When the materials are stretched, they have a tendency to neck down, thereby reducing their effective widths. As they neck down, they tend to form relatively large corrugations or furrows which extend substantially along the direction of stretching. The presence of such corrugations can cause the barrier flaps, particularly the waist flaps, to collapse upon themselves, thereby reducing the ability to remain open to receive and trap bodily waste materials. Additionally, when the conventional materials contract, they tend to decrease in overall stiffness, and this decrease in composite stiffness can again allow the barrier flaps to fold over or collapse upon themselves, thereby reducing their effectiveness.

It has been discovered that particular barrier flap structures, such as laminates incorporating individual and separated elastic strands, can provide structures which can overcome the shortcomings of prior structures. When stretched, the stranded laminates of the invention substantially avoid the undesired stretch-wise corrugating effect typically seen across the plane of the barrier flap and along the intended direction of stretch. Desirably, the amount of stretching does not exceed the amount of elongation at which the elastic strands were assembled into the laminate. When fully stretched and elongated, the stranded laminate can lay substantially flat. As the stranded laminate relaxes and elastically contracts, fine corrugations of sufficient size and frequency can be provided with the furrows or valleys of the corrugate generally aligned to extend substantially perpendicular to the direction of the contraction. The fine corrugations can enhance the stiffness of the flap structure and can improve its ability to remain open to receive waste materials. The stranded laminates of the present invention substantially avoid necking when stretched. Additionally, the geometry of the stranded laminates themselves play an important role in the performance of the materials when employed as a barrier dam structure, such as the shown waist dam and/or containment flap structures. The placement of the strands can also play a role in the functionality of the various configurations of the laminas.

It has been found, however, that the identifications of conventional types of materials or families of materials have not been adequate for deriving barrier flap structures that are sufficiently effective and reliable. It has been discovered that the performance and effectiveness of the barrier flap structure is dependent upon particular combinations of properties and behavior characteristics of the materials employed to assemble and construct the composite barrier flaps. For example, the incorporation of a flap composed of a polyurethane film or film laminate at the article waistband, and the placement of a flap composed of a SMS (spunbond-meltblown-spunbond) nonwoven fabric laminate at the article waistband have not reliably provided a sufficiently effective barrier flap structure. It is important to further configure the materials with particular physical properties, and one of the desired physical properties is the stiffness of the flap member.

The desired stiffness of the barrier flap member can be achieved in a variety of ways. For example, contributing factors include the basis weight of the flap materials, the stiffness or modulus of the individual components, the presence of adhesive added to laminas within the flap member, the pattern and distribution of the applied adhesive, the presence of welding or ultrasonic treatments, the number and the elongation of the individual elastic strands employed in the barrier flap structure, the geometry of the strand placement within barrier flap, the presence and alignment of corrugations within the barrier flap, and the number of layers of components incorporated within the barrier flap.

With reference again to FIGS. 1, 2 and 3, the article of the present invention can include a backsheet layer 30 having a laterally extending width and a longitudinally extending length. The article can also include a porous, liquid permeable topsheet layer 28, which also has a laterally extending width and a longitudinally extending length. The topsheet layer is connected in superposed relation to the backsheet layer 30, and the absorbent body structure 32 is sandwiched and operably secured between the backsheet layer 30 and the topsheet layer 28.

The shown diaper article 10 has a waist pocket member 80 which can include a laterally and longitudinally extending flange section 82, and a laterally and longitudinally extending barrier flap or pocket section 84. The flange section can, for example, be connected to the bodyside surface of the topsheet 28. The flap or pocket section 84 of the waist pocket member 80 includes a substantially fixed edge portion 102 which is secured to the article along and immediately adjacent the boundary of the flange section 82, and includes an elasticized, gathered moveable edge portion 104, which is longitudinally spaced from the fixed edge portion 102 by a selected distance. The pocket section thereby provides an operable waist dam and waist flap construction. The pocket section also includes a substantially liquid impermeable pocket barrier layer 106, and a pocket fabric layer 108 which is connected in facing relation with the pocket barrier layer. The pocket fabric may, for example be composed of a woven or nonwoven fabric, and in the shown arrangement, the fabric layer is desirably a nonwoven. A plurality of separate, laterally extending pocket elastic members 110 are sandwiched and operably connected between the pocket barrier layer 106 and the pocket fabric layer 108 to provide an elasticized waist pocket composite 112, which is gathered substantially along the lateral cross-direction 24 and is elastically stretchable at least along the cross-direction. The shown arrangement includes elastics members which are aligned substantially parallel to one another, but optionally can include other separated configurations and alignments of the elastics. Desirably, the fabric layer 108 is arranged for placement against the wearer's skin, although the barrier layer 106 may optionally be appointed for placement immediately adjacent the wearer's skin.

In a particular aspect of the invention, the flange section 82 of the waist pocket member 80 can include a substantially liquid impermeable flange barrier layer 114, and a flange fabric layer 116 which is operably connected and secured in facing relation with the flange barrier layer. The flange fabric may, for example, be composed of a woven or nonwoven fabric, and in the shown arrangement, and the fabric layer is desirably a nonwoven. A plurality of separate, laterally extending flange elastic members 118 are sandwiched and operably connected between the flange barrier layer 114 and the flange fabric layer 116 to provide an elasticized flange composite 120, which is substantially laterally gathered by the flange elastic members and is elastically stretchable at least along the cross-direction 24. The shown arrangement includes elastics members which are substantially parallel to one another, but optionally can include other separated configurations of the elastics which may be non-parallel. Desirably, the fabric layer 116 is arranged for placement against the wearer's skin, although the barrier layer 114 may optionally be appointed for placement immediately adjacent the wearer's skin. Particular configurations of the flange section 82 can be constructed and arranged to be substantially coterminous with its associated end edge margin 22 of the article.

In particular configurations of the invention, such as the arrangements shown in FIGS. 2 and 3, the pocket section 84 of the waist pocket member 80 can be integrally formed with the flange section 82 of the waist pocket member. In these arrangements, the pocket barrier layer 106 is integrally formed with the flange barrier layer 114 to provide a combined, flange-pocket barrier layer, and the fabric pocket layer 108 is integrally formed with the fabric flange layer 116 to provide a combined flange-pocket fabric layer. The representatively shown arrangement, further includes a flange-pocket barrier layer which is substantially coextensive with the flange-pocket fabric layer.

In other arrangements of the invention, the elastic members 118 in the flange section 82 are spaced from the closest elastic members 110 in the pocket section 84 by a predetermined boundary space 122 which provides a separation distance of at least about 2 mm. In particular aspects, the separation distance provided by the boundary spacing distance is at least about 8 mm, and optionally is at least about 16 mm. The separation distance provides an amount of isolation which effectively permits the flange elastic members to operate substantially separately from the pocket elastic members. Accordingly, the gathering provided by the flange elastics can be substantially separated from the gathering provided by the pocket elastics.

Figure 4:
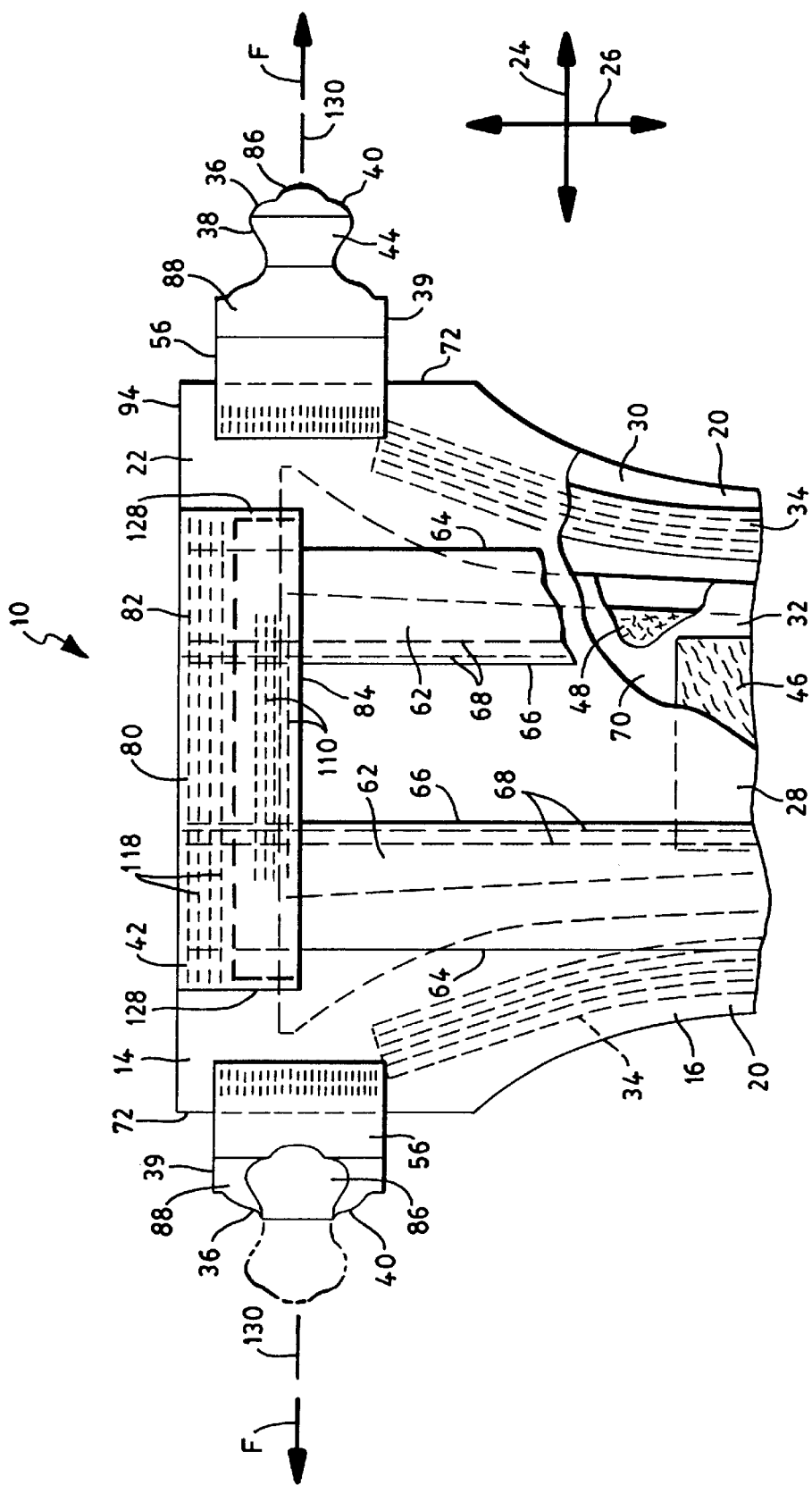
FIG. 4 representatively shows an enlarged, top view of a waistband section of the article of the invention.

With reference to FIGS. 2 and 4, the fastener tabs 36 at the laterally opposed sides of the diaper 10 are desirably substantially aligned along a central, cross-directional alignment line 130. In particular aspects of the invention, the alignment line 130 substantially coincides with, and lies within, the boundary space 122 which separates the set of pocket section elastics 110 from the set of flange section elastics 118 within the waist pocket member 80. In desired configurations, the distal, terminal edge 105 of the pocket section can be aligned with or positioned relatively close to a central force line 130 which is created when a tensioning force, F, is applied to the fastening tabs. Having the distal edge generally aligned with the force line 130 can operably stretch the pocket section 84, particularly the movable edge portion 104 of the pocket section, and can cause the pocket section to stand away from the article. In particular, the pocket section can be more effectively urged to stand away from the bodyside surface of the topsheet 28 during use to create a more effective pocket or waist flap structure to capture bodily fluids and waste. Additionally, the flap structure of the waist pocket section 84 can more effectively maintain contact with the body throughout a range of motions produced by the wearer, and can provide an improved gasket at the region of the movable edge portion 104.

With reference again to FIG. 2, another aspect of the invention can include a configuration in which a one of the elastic members 110 in the pocket section 84 is located most proximally adjacent to the substantially fixed edge portion 102. In addition, such adjacent elastic member is located between the substantially fixed edge portion 102 and the moveable edge portion 104 of the pocket section, and is spaced from the substantially fixed edge portion 102 of the pocket section by a proximal spacing distance 124 which is not less than about 2 mm, and optionally is not less than about 4 mm. In further aspects of the invention the proximal spacing distance 124 is not more than about 13 mm, and optionally is not more than about 8 mm. The proper selection of the spacing distance 124 can help the pocket section 84, particularly its movable edge region, maintain an open position spaced-away from the topsheet of the article. If the distance is too small, the pocket section may not open reliably. If the distance is too great, the pocket section may not adequately resist excessive collapsing.

Figure 6:
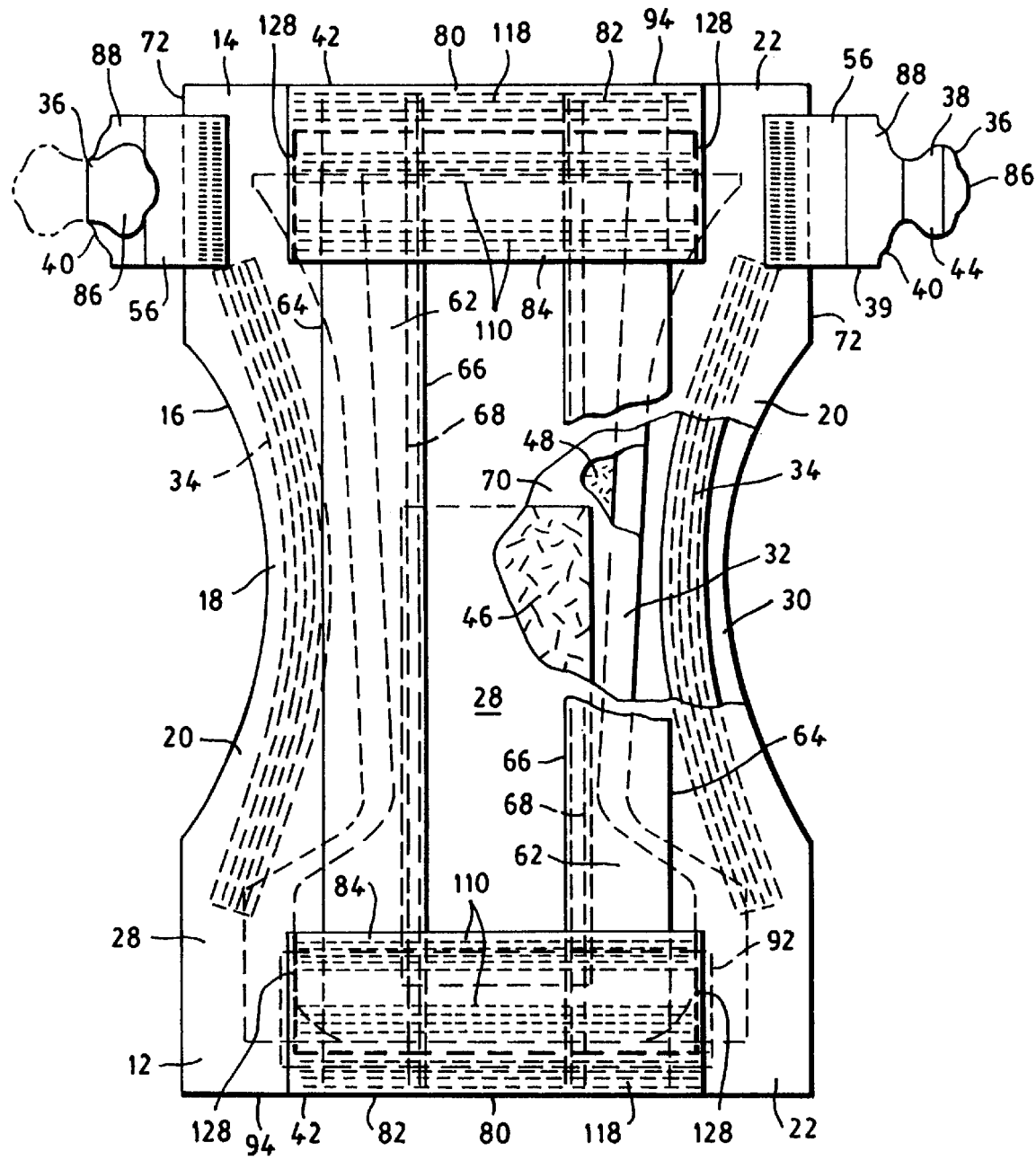
FIG. 6 representatively shows a partially cut-away, top view of another article having dual groupings of elastic strands in the pocket section of the barrier flap system of the invention.

With reference to FIGS. 1, 2 and 3, the pocket section 84 of the waist pocket member 80 can be secured to an appointed region of the article, such as the topsheet 28, by a region of attachment 126. In the shown, arrangement, the attachment 126 extends out of the boundary space 122 to secure the flange section 82 to the topsheet. Optionally, the attachment 126 can be substantially restricted to the boundary space 122, at least within a section of the boundary space 122 which is in a laterally middle or medial portion of the article, and a separate attachment can secure the flange section 82 to the article. Accordingly, the attachment region 126 can operably provide the substantially fixed edge portion 102 of the pocket section 84. In addition, the pocket section 84 of the waist pocket member 80 has laterally opposed end sections 128 which are secured to lie substantially flat against the topsheet 28. As a result, the pocket section 84 of the waist pocket member can be secured to the topsheet 28 with a generally U-shaped arrangement of attachment (FIGS. 1, 4 and 6).

Figure 5:
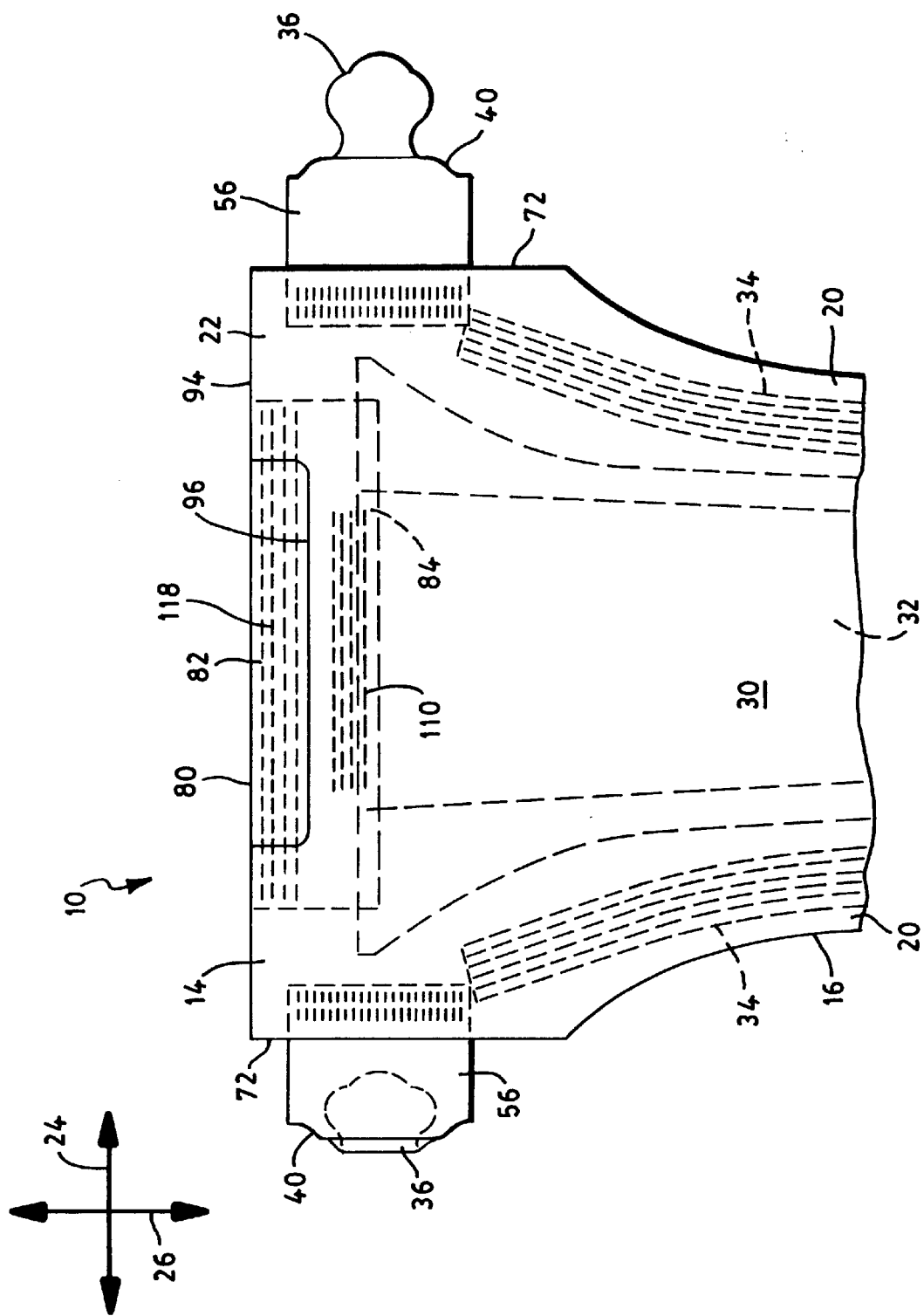
FIG. 5 representatively shows an enlarged, top view of another waistband section of the article of the invention having a notch formed into the waistband of the backsheet.

With reference to FIG. 5, particular configurations of the invention can have the backsheet layer 30 constructed with at least one longitudinally terminal waistband edge 94 which has an inwardly extending notch region 96 formed therein.

The flange section 82 of the waist pocket member 80 is configured and arranged to span across the notch region 96. In addition, the marginal edge portions of the backsheet which are immediately adjacent the notch section can be operably connected and attached to corresponding portions of the flange section.

In the various configurations of the invention, the waistband notch region 96 can have a variety of shapes and sizes. The notch region can have a curvilinear shape, a rectilinear shape, or combinations thereof. Desirably, the waistband notch region 96 can be substantially laterally centered in the cross-directional, medial region of the backsheet 30. In the various arrangements of the invention, the cross-directional extent of the notch region 96 is not more than about 80% of the overall, cross-directional extent of the total article, and desirably is not more than about 40% of the overall, cross-directional extent of the article to provide improved performance. In addition, the cross-directional extent of the notch region 96 can be not less than about 10% of the overall, cross-directional extent of the article, and desirably is not less than about 20% of the overall, cross-directional extent of the article to provide desired levels of comfort and waste containment. In still other aspects, the longitudinal or depth extent of the notch region 96 is within the range of about 2–15% of the overall longitudinal extent of the total article. In a diaper-type article, for example, the notch region 96 can have a maximum, longitudinally inward extent of at least about 9 mm. Alternatively, the inward extent of the notch region 96 is at least about 12.5 mm, and optionally is at least about 15 mm. In other arrangements, the inward extent of the notch region 96 is not more than about 65 mm. Alternatively, the maximum inward extent can be not more than about 55 mm, and optionally can be not more than about 45 mm. When measuring the dimensions of the notch region 96, the article is placed in its substantially flat-out, uncontracted condition with the elastic gathers at the article waistband substantially removed.

With reference to FIGS. 2 and 3, a one of the pocket elastic members 110 is located most proximally adjacent to the terminal edge 105 of the moveable edge portion 104 of the pocket section 84 and is spaced from the terminal edge by a spacing distance 107 of not more than about 13 mm. Alternatively, the edge spacing distance is not more than about 7 mm, and optionally is not more than about 1 mm. In a further aspect, the terminal edge 105 is substantially unfolded. In particular, the terminal edge portion of the pocket section is not folded back upon itself to envelop and enclose one or more of the pocket elastics. The positioning of elastic members proximate the distal, terminal edge 105 can help to maintain the open position of the pocket section 84 across substantially the full width of the pocket section. As a result, the pocket section can better provide a functional barrier dam structure.

The various arrangements of the invention can also be constructed to provide the flange and pocket sections 82 and 84, respectively, with desired stiffness values. In particular, either or both of the flange and pocket sections can have a stiffness value which is at least about 5 mg. Alternatively, the stiffness can be at least about 15 mg, and optionally, can be at least about 30 mg to provide improved performance. In other aspects of the invention, either or both of the flange and pocket sections can have a stiffness which is not more than about 250 mg. Alternatively, the stiffness can be not more than about 200 mg, and optionally, can be not more than about 170 mg to provide improved performance. Where the stiffness is too low, the pocket section can be excessively susceptible to collapsing. Where the stiffness is too high, the pocket or flange sections may cause excessive irritation to the wearer.

The stiffnesses of the various components and sections of the article of the invention can be determined by employing the test methodology of TAPPI T543 om-94, and by employing a Gurley Digital Stiffness tester, Model 4171-D, a device available from Teledyne Gurley, a business having offices located in Troy, N.Y. Accordingly, the stiffness values of the various sections of the article, such as the waist pocket member 80, are bending stiffnesses. The stiffnesses can be expressed as milligrams (mg) which correspond to Standard Gurley Units of milligrams-force. For the purposes of the present invention, the axis about which a bending moment is applied to the sample during the stiffness testing is a bending axis which Is aligned substantially parallel to the direction of elastic stretch and gathering provided by the associated elastic members, such as elastic members 110 and/or 118. With regard to the stiffness testing of the pocket section 84, for example, the bending axis of the test sample of the pocket section would be along an axis line which would have been substantially aligned with the article cross-direction 24, as observed when the pocket section was originally assembled in the article.

In regard to either or both of the flange section 82 and pocket section 84 of the waist pocket member 80, the barrier layer can be provided by polymer films or fabrics having low permeability to liquid, and combinations thereof. Polymer films may, for example, be composed of polyolefins, polyesters, polyamides and the like. Nonwoven materials can include spunbond-meltblown-spunbond (SMS) fabrics, meltblown fabrics, calendered nonwoven sheets and the like. With respect to the passage of liquid through its thickness, the barrier layer is constructed to exhibit a hydrohead of resistance which is sufficient to provide an effective barrier against the passage liquids, such as urine.

For example, the barrier layer may be composed of a 0.0006 inch (0.015 mm) cast, embossed film, such as a CT (XEM400.1), or a 0.0004 inch (0.010 mm) blown film, such as XSF-367, available from Consolidated Thermoplastics, a business having offices located in Chippewa Falls, Wis. The barrier layer may also be a 0.00035 inch (0.0089 mm) stretch-thinned film, such as XP1024A, available from Edison Plastics a business having offices located in Macalester, Okla.

With regard to either or both of the flange section 82 and pocket section 84 of the waist pocket member, the fabric layers 108 and/or 116 can be composed of a fine denier, low basis weight nonwoven material. Examples of such nonwoven fabrics include polypropylene spunbond materials, bicomponent polypropylene/polyethylene spunbond materials, meltblown materials, SMS materials, through-air-bonded carded webs, point-bonded bonded-carded webs, and the like.

For example, the fabric layer may comprise a 0.5 oz/yd$^2$ (17 gsm) polypropylene spunbond fabric composed of fibers having denier of less than about 4 den. The fabric layer can alternatively have fibers with deniers of less than about 3 den, and optionally can include fibers having deniers of less than about 2.5 den.

Either or both of the pocket elastic members 110 and flange elastic members 118 can be composed of strands of natural or synthetic elastomeric materials, such as natural or synthetic rubbers. In particular aspects of the invention, the elastic members can include strands having a denier of not less than about 100 denier. Alternatively, the elastic members can have a denier of not less than about 280, and optionally can have a denier of not less than about 360. In other aspects of the invention, the elastic members can include strands having a denier of not more than about 1920 den. Alternatively, the elastic members can have a denier of not more than about 1140 den, and optionally can have a denier of not more than about 560 den. For example, the pocket elastic members 110 and/or the flange elastic members 118 can include 360 denier GLOSPAN S7 elastic strands available from Globe Manufacturing Co.

To produce the flange and pocket sections of the waist pocket member 80, the pocket elastics and/or the flange elastics can be elongated 25–350 percent (as determined with respect to the unstretched length of the elastics) prior to assembly into the waist pocket member to form the pocket composite 112 and/or the flange composite 120. For example, the flange elastics 118 can be configured with about 150 percent elongation, and the pocket elastics 110 can have an elongation of about 175 percent.

The number of elastic strands and the spacing between the strands can be selected and arranged to provide desired performance. For example, the elastics can be selectively configured to provide a desired gasketing function against the wearer's skin while avoiding excessive irritation and redmarking of the wearer's skin.

In particular aspects of the invention, the number of elastic strands in each of the flange section 82 and/or pocket section 84 can be at least about 2, and alternatively is at least about 3. In further aspects of the invention, the number of elastic strands in each of the flange section and/or pocket section can be not more than about 25. Alternatively, the number of elastic strands in each of the sections can be not more than about 20, and optionally can be not more than 15. Laminates with too many strands across the longitudinal depth of the pocket section can undesirably cause the flap structure to lay closed, substantially flat against the topsheet of the article, while laminates having too few strands can excessively collapse and fold in upon themselves. The appropriate number of strands, the appropriate spacing between strands, the appropriated elongation of the strands, and the appropriate spacing of the strands from the fixed and movable edges of the pocket section are dependent upon the physical properties of the individual laminate components, as well as the dimensions of the flaps.

In other aspects of the invention, the elastic members of the flange section 82 and/or pocket section 84 can have an elastic spacing distance 132 which is at least about 2 mm. Alternatively, the elastics spacing distance 132 can be at least about 3 mm, and optionally can be at least about 4 mm. In further aspects, the elastic members of the flange section 82 and/or pocket section 84 can have an elastic spacing distance 132 which not more than about 13 mm. Alternatively, the elastics spacing distance 132 can be not more than about 11 mm, and optionally can be not more than about 8 mm to provide improved control over the operation of the barrier flap structure.

To further control the operation of the barrier flap structure, such as the pocket section 84, the pocket elastic members 110 may be uniformly spaced across the entire width of the lamina (as determined along a dimension which is substantially perpendicular to the stretching dimension of the elastic member), or they may be grouped into discrete and distinct functional sets. For example, FIG. 6 representatively shows a laminate having more than one functional groupings of pocket elastics 110. Such multiple grouping may be placed in either or both of the pocket or flange sections of the waist pocket member 80 to control the operation of the barrier flap and to enhance performance.

In particular aspects of the invention, the flange elastic members 118 can be arranged to provide for a flange contractive force and the pocket elastic members can be arranged to provide for pocket contractive force. In a particular aspect of the invention, the contractive force exerted by the flange elastics is configured to be relatively greater than the contractive force exerted by the pocket elastics. As representatively shown in FIGS. 1 and 4, for example, the flange elastics can be longer, or otherwise larger or more strongly contracted, than the pocket elastics. Such an arrangement can provide a desired relative contraction between the flange and pocket sections of the waist pocket member 80 when the waist pocket is operably assembled to the final article, and can help maintain a desired, open condition of the pocket section 84 during use on the wearer.

In a desired aspect of the invention, the elastic members in either the waist flange region, the pocket region or both regions may be operably zone-tensioned, as representatively shown in FIGS. 1 and 4. Desirably, the zone tensioning is configured to substantially limit the elasticized gathering to a medial, laterally-central region of the waist pocket member. The zone tensioning may be achieved in a variety of ways. For example, an adhesive or other bonding mechanism may be applied only in the areas where the retraction of the elastic members is intended to gather the flap composite. In the regions where the bonds are absent, the remaining elastic members can contract substantially without gathering the flap composite. Alternatively, other techniques, such as ultrasonics, can be employed to operably deaden the elastic members in the regions where elastic retraction is not desired.

The elastomeric members 110 and/or 118 can be attached to either or both of their associated barrier and fabric layers with a suitable securing means, such as a selected pattern of adhesive or other type of bonding. For example, the adhesive may be applied by spraying adhesive discontinuous droplets or filaments, and/or may be applied by arranging generally continuous lines of adhesive in a selected pattern, such as a swirl pattern. Alternatively, the elastomeric members 110 and/or 118 can be attached to at least one of the barrier and fabric layers with a plurality of individual, longitudinally extending strips of adhesive. Each individual adhesive strip is spatially separated from immediately adjacent adhesive strips by a discrete distance, and each individual adhesive strip is arranged to attach substantially an individual one of the elastomeric members to the at least one of the barrier and fabric layers. In the shown arrangements, for example, the strips of adhesive can be aligned substantially parallel to one another.

With reference to FIGS. 1 through 4, the pocket section 84 of the waist member 80 may be configured to bridge and span over the inward facing, bodyside surfaces of the longitudinally extending containment flaps 62. Desirably, the movable edge portions 104 of the pocket section 84 are substantially unconnected and unattached to the distal, movable edges 66 of the containment flaps 62 to thereby reduce interaction between the elasticized containment flaps 62 and the elasticized pocket section 84. In addition, it is desirable to zone the elastic tension exerted by the elastic members 68 employed to elasticize the containment flaps 62. More particularly, the elastic tension in the containment flaps is substantially restricted to a longitudinally medial section of each containment flap. Accordingly, the end regions of each containment flap, particularly the end regions generally adjacent to the pocket section 84, are substantially free of elastic tension exerted by the elastic members 68. The distal edges 66 can also be secured to the topsheet layer 28 with a suitable attaching mechanism to further isolate the distal edges 66 of the containment flaps away from the operation and opening of the pocket section 84.

The above-described zoned tensioning of the containment flaps 62 can be achieved in a variety of ways. For example, the elastic contractibility of the elastic members 68 in the appropriate end regions of the containment flaps can be operably deadened, such as by a mechanical, ultrasonic or thermal treatment which effectively "kills" or otherwise deactivates the elasticity or contractibility in the selected regions. Alternatively, the elastic members 68 in the end regions of the containment flaps may be substantially unattached to the containment flap material. Accordingly, the elastic members at the containment flap end regions can elastically retract substantially without exerting a gathering tension onto the end regions of the containment flaps 62. In further configurations, the distal end regions of the containment flaps can be substantially, entirely immobilized, such as by operably securing the end regions onto the topsheet layer 28 with adhesive, sonic bonds or other attaching mechanisms.

With reference to FIGS. 7 and 8, each of the leg elastics can alternatively be provided by a distinctive leg gusset members 19. More particularly, the article of the invention can be configured with each leg gusset 19 connected directly or indirectly to an appointed section of an inwardly facing, bodyside surface of the topsheet layer 28. Optionally, the leg gusset can be connected directly or indirectly to an appointed surface region of the backsheet layer 30. In particular, each leg gusset is connected along its associated, outwardly concave, terminal side edge contour 15, and each of the side edge contours can have a longitudinal length 54 which desirably extends completely through the crotch region 18, and which may extend along at least about 20 percent of a total longitudinal length 180 of the article. In further configurations, the longitudinal length 54 can be at least about 30 percent, alternatively can be at least about 40 percent, and optionally can be up to 100 percent of the total longitudinal length 180 of the article.

Each leg gusset 19 can have a length 178 thereof which extends along at least about 20 percent of the total longitudinal length 180 of the article. In other configurations, each leg gusset 19 can extend along at least about 30 percent, and alternatively at least about 40 percent of the longitudinal length 180 of the article to provide improved effectiveness. If desired, each leg gusset can extend along a length which can be up to 100 percent of the total longitudinal length of the article to provide further gasketing and containment. Alternatively, each leg gusset can extend along a length which is not more than about 80 percent, and optionally is not more than about 70 percent of the total longitudinal length of the article to provide desired performance.

Additionally, each leg gusset 19 can be in a bridging configuration across its associated, concave side edge contour 15 of the backsheet layer along a length 182 which is at least about 20 percent of the longitudinal length 180 of the article. In other configurations, each leg gusset 19 can be in a bridging configuration across its associated, concave side edge contour 15 of the backsheet layer along a length 182 which is at least about 30 percent, and alternatively is at least about 40 percent of the extent of the longitudinal length 180 of the article to provide improved effectiveness. If desired, each leg gusset can be in a bridging configuration along a length which can be up to 100 percent of the total longitudinal length of the article to provide further gasketing and containment. Alternatively, each leg gusset can be in a bridging configuration along a length which is not more than about 80 percent, and optionally is not more than about 70 percent of the total longitudinal length of the article to provide desired performance and cost effectiveness.

In particular aspects of the invention, the leg gussets 19 are configured to substantially avoid intersecting the locations of the waist pocket members 80. Accordingly, the leg gussets can be constructed to terminate at positions which are spaced away from the terminal edges of the pocket sections 84 of the waist pocket members.

With reference to FIG. 8, each of the side margins of the backsheet layer 30 generally defines a plane thereof, and each of the leg gussets 19 is constructed to extend past and beyond its associated concave side edge contour 15 of the backsheet layer 30 by a selected skirting distance 184, and in an arrangement which lies substantially within and substantially parallel to the plane of its associated backsheet side margin.

In the various arrangements of the invention, each leg gusset 19 can include a substantially liquid impermeable barrier layer 134, a nonwoven fabric layer 136 and a plurality of separate, longitudinally extending elastomeric members 138 sandwiched between the gusset barrier layer and the gusset fabric layer to provide an elastomeric composite which is substantially longitudinally gathered. In particular arrangements, the barrier layer 134 and the fabric layer 136 can be substantially coextensive. The elastomeric members can be arranged in any desired alignment or configuration, such as parallel, non-parallel, straight, curvilinear or combinations thereof. Desirably, the fabric layer 136 is arranged for placement against the wearer's skin, although the barrier layer 134 may optionally be appointed for placement immediately adjacent the wearer's skin.

The gusset barrier layer 134 can be composed of a variety of materials, such as polymer films, fabrics or combinations thereof, having a relatively low permeability to aqueous liquid. The polymer films may, for example, be composed of polyolefins, polyesters, polyamides and the like. The fabrics may be woven or nonwoven, and the nonwoven materials can include spunbond-meltblown-spunbond (SMS) fabrics, meltblown fabrics, calendered nonwoven sheets and the like. With respect to the passage of liquid through its thickness, the barrier layer is constructed to exhibit a hydrohead of resistance which is sufficient to provide an operably effective barrier against the passage liquids, such as urine.

In particular, the gusset barrier layer can be composed of a cast, embossed film having a thickness of about 0.015 mm (about 0.0006 inch), such as a CT XEM400.1 film; or a blown film having a thickness of about 0.010 mm (about 0.0004 inch), such as an XSF-367 film. Suitable films are available from Consolidated Thermoplastics, a business having offices in Chippewa Falls, Wis. The barrier layer may also be composed of a stretch-thinned film having a thickness of about 0.0089 mm (about 0.00035 inch), such as an XP1024A film available from Edison Plastics, a business having offices in Macalester, Okla.

The gusset fabric layer 136 can be composed of a variety of materials, such as a fine denier, low basis weight, nonwoven fabric material. Examples of suitable nonwoven fabrics include polypropylene spunbond materials, bicomponent polypropylene-polyethylene spunbond materials, meltblown materials, SMS materials, through-air-bonded carded webs, point-bonded bonded-carded webs and the like.

In desired arrangements, the fabric layer 136 can have a basis weight of not less than about 3.4 g/m$^2$ (about 0.1 oz/yd$^2$). Alternatively, the basis weight can be not less than about 10.2 g/m (about 0.3 oz/yd$^2$), and optionally can be not less than about 13.6 g/m$^2$ (about 0.4 oz/yd$^2$). In other aspects, the fabric layer 136 can have a basis weight of not more than about 272 g/m$^2$ (about 8 oz/yd$^2$). Alternatively, the basis weight can be not more than about 136 g/m$^2$ (about 4 oz/yd$^2$), and optionally can be not more than about 34 g/m$^2$ (about 1 oz/yd$^2$).

For example, the gusset fabric layer can be a nonwoven fabric composed of polypropylene fibers wherein the fiber denier is not more than about 4 denier, and the fabric basis weight is about 17 g/m$^2$ (about 0.5 oz/yd$^2$). Alternatively, the fiber denier in the fabric layer can be not more than about 3 denier, and optionally can be not more than about 2.5 denier.

In particular aspects of the invention, the leg gusset 19 can have a composite stiffness which is not less than about 5 mg. The composite stiffness can alternatively be not less than about 10 mg, and optionally can be not less than about 15 mg. In other aspects of the invention, the leg gusset 19 can have a composite stiffness which is not more than about 250 mg. The composite stiffness can alternatively be not more than about 200 mg, and optionally can be not more than about 170 mg.

For the purposes of the present invention, the stiffness of the leg gusset 19 is taken with respect to the cross dimension of the article. The stiffness is determined with respect to a bending moment which is applied about a bending axis that is generally aligned along the longitudinal dimension 26 of the article.

In further aspects of the invention, the elastic members 138 of the leg gusset 19 are attached to at least one of the barrier and fabric layers with a selected pattern of adhesive. In particular arrangements, elastic members 138 are attached with a plurality of individual strips of adhesive. Each individual adhesive strip is spatially separated from immediately adjacent adhesive strips by a discrete distance, and each individual adhesive strip is configured to attach substantially a one of the elastomeric members 138 to be at least one of the barrier and fabric layers.

In another aspect of the invention, adjacent elastomeric members 138 can have a spacing distance 139 therebetween which is not less than about 2 mm. Alternatively, the spacing distance can be not less than about 3 mm, and optionally can be not less than about 4 mm. In further aspects of the invention, the adjacent elastomeric members 138 can have a spacing distance 139 therebetween which is not more than about 13 mm. Alternatively, the spacing distance can be not more than about 11 mm, and optionally can be not more than about 8 mm.

The elastomeric members 138 within each leg gusset 19 can be configured to provide for a composite elastic tension which is not less than about 50 grams-force when the leg gusset composite is stretched to a length which is 90 percent of its substantially flat-out, uncontracted, extended length. The composite elastic tension can alternatively be not less than about 75 grams-force and optionally can be not less than about 100 grams-force to provide an improved combination of comfort and containment. In other aspects of the invention, the elastomeric members 138 within each leg gusset 19 can be configured to provide for a composite elastic tension which is not more than about 300 grams-force when the leg gusset composite is stretched to 90 percent of its flat-out, uncontracted length. The composite elastic tension can alternatively be not more than about 250 grams-force and optionally can be not more than about 200 grams-force to provide desired combinations of comfort and containment.

In the various configurations of the invention, each leg gusset 19 can have a lateral width 186 which is not less than about 13 mm. The lateral width of the leg gusset can alternatively be not less than about 19 mm, and optionally can be not less than 25 mm. In further aspects of the invention, each leg gusset 19 can have a lateral width 186 which is not more than about 104 mm. The lateral width of the leg gusset can alternatively be not more than about 76 mm, and optionally can be not more than about 51 mm.

In desired configurations, each leg gusset 19 can extend laterally beyond its associated side edge contour 15 of the backsheet layer 30 by a skirting distance 184 of not less than about 3 mm. Alternatively, the skirting distance can be not less than about 6 mm and optionally can be not less than about 9 mm, at least within the crotch section 18 of the article. In other aspects of the invention, each leg gusset 19 can extend laterally beyond its associated side edge contour 15 of the backsheet layer 30 by a skirting distance of not more than about 51 mm. Alternatively, the skirting distance 184 can be not more than about 35 mm, and optionally can be not more than about 20 mm, at least within the crotch section 18 of the article, to provide improved comfort and gasketing.

The various configurations of the leg gusset 19 can provide a plurality of separate, longitudinally extending elastomeric members which are laterally spaced outboard from said backsheet layer by a discrete distance, at least within the crotch region of the article. Such laterally spaced elastomeric members can substantially avoid having a direct connection to said backsheet layer and can substantially avoid providing a direct gathering of said backsheet layer in its crotch region.

As representatively shown in FIGS. 7 and 8, each leg gusset 19 is connected to the article, particularly with the bodyside surface of topsheet 28, with a gusset attachment 172, which holds the leg gusset 19 substantially parallel to a plane generally defined by its associated side margin of the backsheet 30. More particularly, the gusset attachment 172 includes an article attachment which secures the leg gusset 19 to the article adjacent to its associated outwardly concave terminal side edge contour 15 of the backsheet layer 30 along substantially an entire length of the side edge contour within which the leg gusset 19 and its associated side edge contour 15 are coextensive. In particular aspects of the invention, the securement of each leg gusset to the article substantially ends at a location which is laterally outboard of the absorbent body structure 32, at least within the crotch portion 18 of the article. Accordingly, the securement of the leg gusset to the crotch portion article substantially ends at a location which is laterally outboard of the retention portion 48. Additionally, the securement of the leg gusset to the crotch portion of the article can substantially end at a location which is laterally outboard of the wrapsheet 70. In the shown arrangements, for example, the leg gusset attachment 172 has a generally U-shape configuration, with the bottom of the U-shape extending generally longitudinally and the two arms of the U-shape extending generally laterally. The shown U-shape is angular, but may be non-angular, if desired.

The various configurations of the invention can include two or more cooperating leg gussets 19, such as the shown laterally opposed pair of leg gussets. With respect to each other, the leg gussets can be arranged to be parallel or non-parallel, and each leg gusset can be straight and/or curvilinear.

In another aspect of the invention, each leg gusset 19 includes a plurality of two or more separate, longitudinally extending elastomeric members 138 which are laterally spaced outboard from the side edge contour 19 of the backsheet layer 30 by a discrete distance, at least within the crotch region 18 of the article. In desired arrangements, the laterally spaced elastomeric members substantially avoid having a lamination onto or other direct or immediate connection to the backsheet layer 30 and thereby substantially avoid providing a direct gathering of the backsheet layer, at least within the crotch region 18 of the article.

Figure 10:
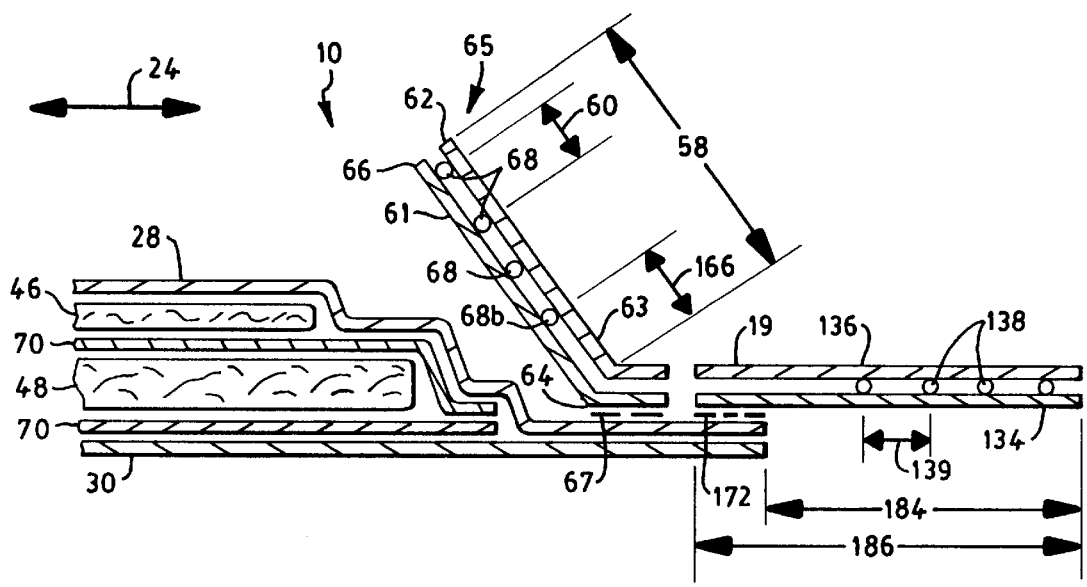
FIG. 10 a schematic, expanded, lateral cross-sectional view of one of the leg gusset members and its adjacent containment flap, taken through the crotch section of the article.
Figure 9:
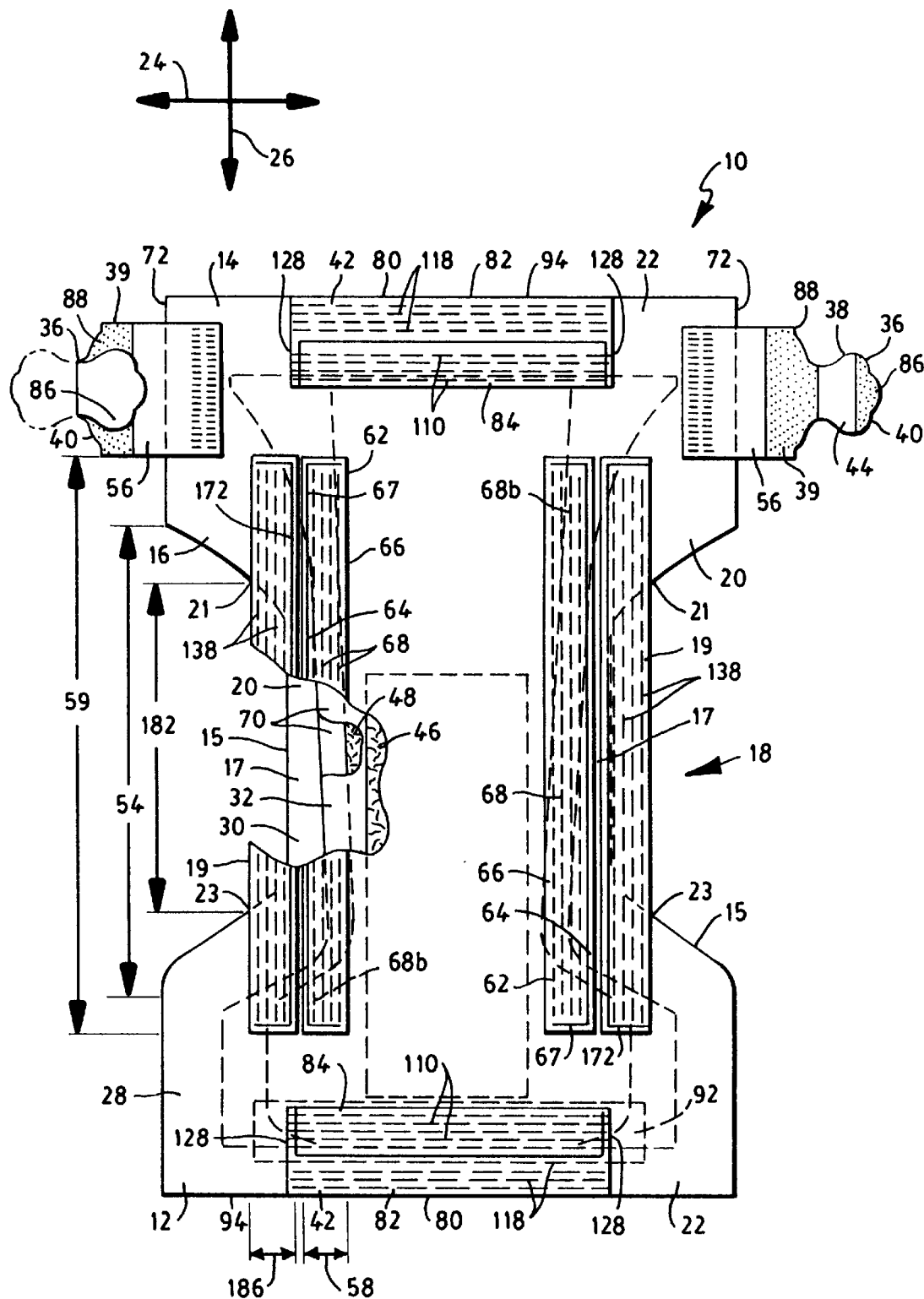
FIG. 9 representatively shows a partially cut-away, top view of another article of the invention having a laterally opposed pair of leg gusset members and a laterally opposed pair of laminated containment flaps.

With reference to FIGS. 9 and 10, the various configurations of the invention can provide an absorbent article, such as diaper 10, having a longitudinal length dimension 26, a lateral cross dimension 24, a front waistband portion 12, a back waistband portion 14, an intermediate portion 16 which interconnects the front and back waistband portions, and a pair of elasticized laterally opposed leg opening regions 17. The article includes a backsheet layer 30, and a liquid permeable topsheet layer 28 connected in a superposed relation to the backsheet layer. An absorbent body structure 32 is sandwiched between the topsheet layer 28 and the backsheet layer 30, and a pair of elasticized and gathered, laterally opposed and longitudinally extending containment flaps 62 are connected to at least one of the backsheet and topsheet layers. Each containment flap 62 has a movable edge portion 66 and a substantially fixed edge portion 64 located proximally adjacent to a one of the elasticized leg openings 17, at least in the crotch section 18 of the article. In particular configurations of the invention, each containment flap 62 can include a substantially liquid impermeable barrier layer 61 and a nonwoven fabric layer 63 connected in a superposed, facing relation with the barrier layer 61. A plurality of separate, longitudinally extending elastomeric members 68 can be sandwiched between the barrier layer 61 and the fabric layer 63 to provide an elastomeric composite 65 which is substantially longitudinally gathered. In particular arrangements, the barrier layer 61 and the fabric layer 63 can be substantially coextensive. Desirably, the fabric layer 63 is arranged for placement against the wearer's skin, although the barrier layer 61 may optionally be appointed for placement immediately adjacent the wearer's skin.

In desired arrangements of the containment flaps, the barrier layer 61 can be composed of any of the materials suitable for forming the barrier layer 134 of the leg gussets 19. Similarly, the fabric layer 63 of the containment flaps can be composed of any of the materials suitable for forming the fabric layer 136 of the leg gussets.

Each containment flap 62 includes at least one of the elastomeric members 68 attached to the containment flap at a location which is proximate a movable edge 66 of the containment flap. In particular configurations, at least one of the elastomeric members 68 is attached to the containment flap at a location which is proximate a substantially fixed edge 64 of the containment flap.

With reference to FIG. 10, each containment flap 62 can include at least one base elastomeric member 68*b* which is attached to the containment flap 62 at a location which is between the movable edge portion 66 and the substantially fixed edge 64 of the containment flap, and has a spacing distance 166 which is not more than about 8 mm from the fixed edge 64 of the containment flap, at least within the crotch portion 18 of the article. In particular arrangements, the at least one base elastomeric member 68*b* can be attached substantially immediately adjacent to the fixed edge 64 of the containment flap 62.

In particular aspects of the invention, each containment flap 62 has a composite stiffness of at least about 5 mg, taken with respect to the cross dimension of the article. For the purpose of the present invention, the stiffness of the containment flap is determined with respect to a bending moment which is applied about a bending axis that is substantially aligned along the longitudinal dimension 26 of the article. Desirably, the containment flap has a composite stiffness which is not less than about 10 mg, and alternatively, is not less than about 15 mg to provide improved containment. In further aspects, the containment flap can have a composite stiffness which is not more than about 250 mg. The composite stiffness can alternatively be not more than about 200 mg, and optionally can be not more than about 170 mg to provide desired performance. If the stiffness of the containment flap 62 is too low, the containment flap may excessively collapse upon itself. If the stiffness of the containment flap is too high, there may be excessive irritation of the wearer's skin.

The containment flap elastomeric members 68 can be attached to at least one of the barrier and fabric layers, 61 and 63, respectively, with a suitable securing means, such as a selected pattern of adhesive or other type of bonding. For example, the adhesive may be applied by spraying adhesive discontinuous droplets or filaments, and/or may be applied by arranging generally continuous lines of adhesive in a selected pattern, such as a swirl pattern. Alternatively, the elastomeric members 68 can be attached to at least one of the barrier and fabric layers with a plurality of individual, longitudinally extending strips of adhesive. Each individual adhesive strip is spatially separated from immediately adjacent adhesive strips by a discrete distance, and each individual adhesive strip is arranged to attach substantially an individual one of the elastomeric members 68 to the at least one of the barrier and fabric layers. In the shown arrangements, for example, the strips of adhesive can be aligned substantially parallel to one another.

In particular aspects of the invention, adjacent elastomeric members 68 can have a spacing distance 60 which is not less than about 2 mm. The spacing distance between adjacent elastomeric members 68 can alternatively be not less than about 3 mm, and optionally can be not less than about 4 mm. In other aspects, the adjacent elastomeric members 68 can have a spacing distance 60 which is not more than about 13 mm. The spacing distance between adjacent elastomeric members 68 can alternatively be not more than about 11 mm, and optionally can be not more than about 8 mm to provide desired effectiveness.

In desired arrangements, each containment flap 62 can have a lateral width dimension 58 of at least about 13 mm. In addition, each containment flap 62 may have a longitudinal length 59 which is substantially equal to the overall, total length 180 (FIG. 7) of the article. Alternatively, each containment flap may have a length which is less than the overall, total length of the article, and the shorter containment flap may be configured with a zoned-placement at a selected location along an appointed portion of the overall length of the article. For example, the length of the containment flap may be substantially centrally located along the article length, or may be positioned with an offset toward the front or back waistband of the article. Optionally, each containment flap may have a length which is substantially equal to or less than the overall, total length of the absorbent body structure 32, and the relatively shorter containment flap may be configured with a zoned-placement at a selected location along an appointed portion of the overall length of the absorbent body structure.

The containment flaps 62 are operably secured to appointed sections of the article, such as laterally opposed sections of the topsheet layer 28, with a suitable attachment mechanism 67. In the shown arrangements, for example, the containment flap attachments can be similar to those employed with the waist pocket member 80 and with the leg gussets 19. The attachments can have a generally U-shape configuration, with the bottom of the U-shape extending generally longitudinally and the two arms of the U-shape extending generally laterally. The shown U-shape is angular, but may be non-angular, if desired.

Figure 11:
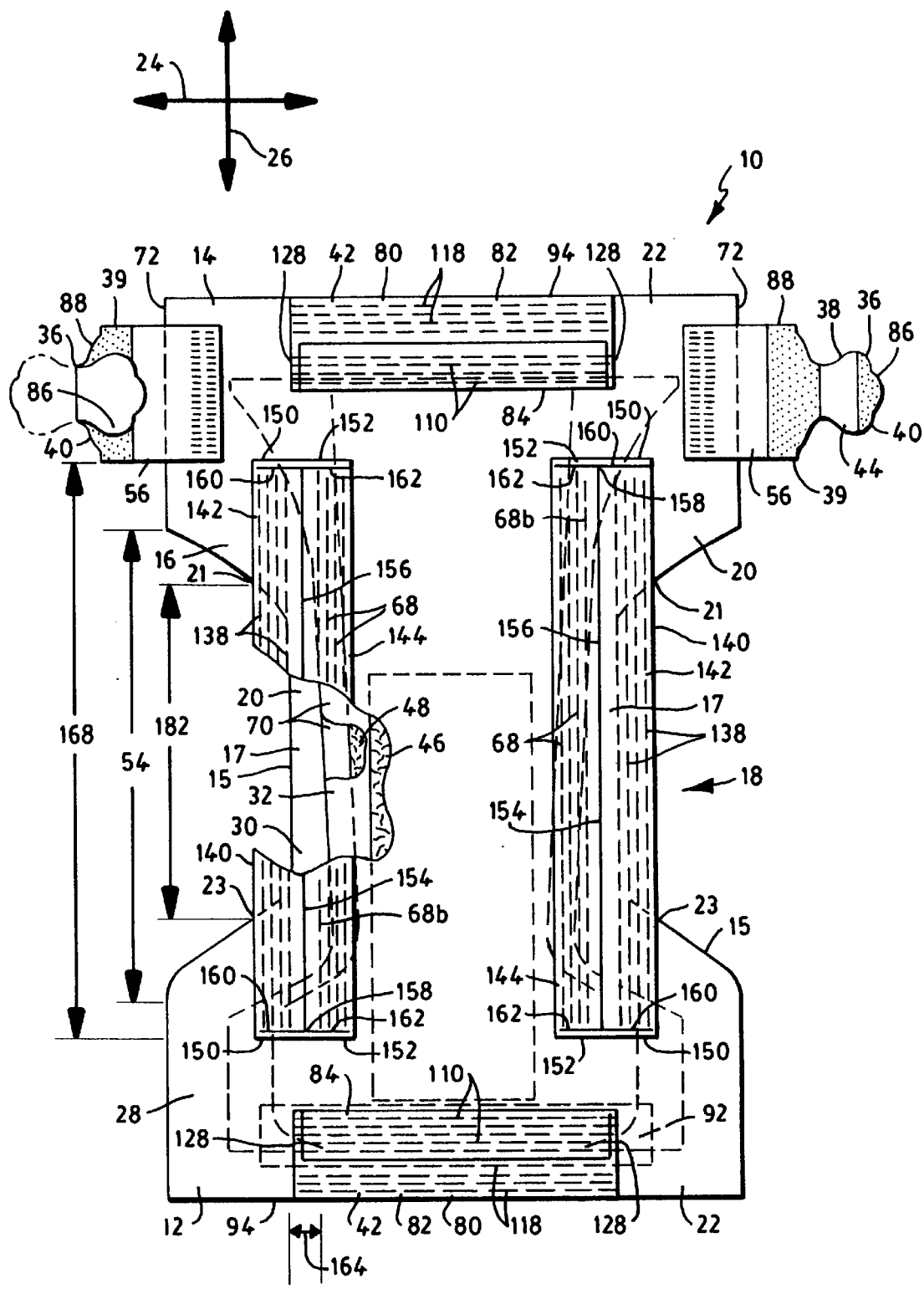
FIG. 11 representatively shows a partially cut-away, top view of another article of the invention having a laterally opposed pair of combined and integrated, gusset-flap members.
Figure 12:
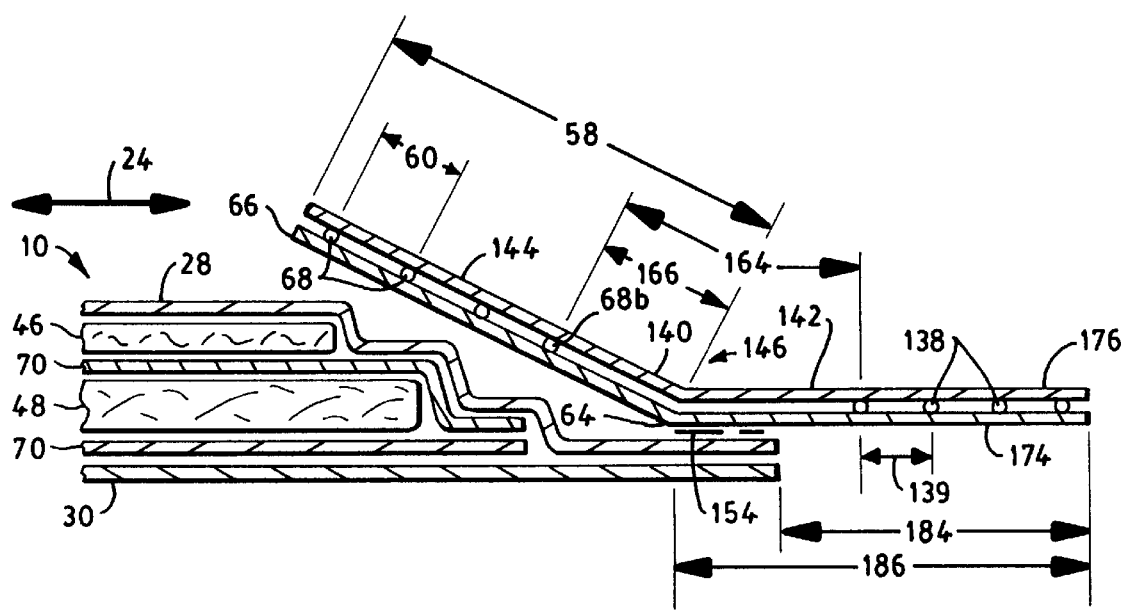
FIG. 12 a schematic, expanded, lateral cross-sectional view of one of the gusset-flap members taken through the crotch section of the article.

As representatively shown in FIGS. 11 and 12, other aspects of the invention can provide an absorbent article, such as diaper 10, having a longitudinal length dimension 26, a lateral cross dimension 24, a front waistband portion 12, a back waistband portion 14, and an intermediate portion 16, which interconnects the front and back waistband portions. The article includes a backsheet layer 30 having a pair of laterally opposed side margins. Each side margin has a selected terminal side edge contour, such as the shown outwardly concave, terminal side edge contour 15, located at appointed leg openings regions 17 in an intermediate portion of each of the side margins. Each concave side edge contour 15 has a selected longitudinal extent along the length dimension of the article. A liquid permeable topsheet layer is connected in a superposed facing relation to the backsheet layer 30, and an absorbent body is sandwiched and operably attached between the topsheet layer 28 and the backsheet layer 30. A separate gusset-flap member 140 is connected to at least one of the backsheet and topsheet layers along each of the appointed leg opening regions 17. The gusset-flap member 140 includes a leg gusset section 142 and a containment flap section 144. Each leg gusset section 142 is configured to extend beyond and bridge across its associated, outwardly concave terminal side edge contour 15 of the backsheet layer 30, and each leg gusset section 142 provides an elasticized and gathered outboard side margin of the article. Each containment flap section 144 is desirably integrally formed with or otherwise integrally attached to a one of the leg gusset sections 142 to provide a gusset-flap composite 146. Each containment flap section 144 has a substantially fixed edge 64 located proximally adjacent to a one of the elasticized side margins, and has an elasticized and gathered, distal, movable edge portion 66. Each gusset-flap member 140 includes a substantially liquid impermeable barrier layer 174, and a nonwoven fabric layer 176 which is substantially coextensive with the barrier layer 174. The fabric layer 176 is connected in a superposed, facing relation with the barrier layer. A plurality of separate, longitudinally extending elastomeric members 68 and 138 are sandwiched between the gusset-flap barrier layer 174 and the gusset-flap fabric layer 176 to provide an elastomeric or otherwise elasticized gusset-flap composite 146 which is substantially longitudinally gathered.

In other arrangements of the invention, the elastic members 68 in the containment flap section 144 are spaced from the closest elastic members 138 in the gusset section 142 by a predetermined boundary space 164 which provides a separation distance of at least about 2 mm. In particular aspects, the separation distance provided by the boundary spacing distance is at least about 8 mm, and optionally is at least about 16 mm. The separation distance provides an amount of isolation which effectively permits the containment flap elastic members 68 to operate substantially separately from the gusset elastic members 138. Accordingly, the gathering provided by the containment flap elastics can be substantially separated from the gathering provided by the gusset elastics.

In the gusset-flaps 140, the barrier layer 174 can be composed of any of the materials suitable for forming the barrier layer 134 of the leg gussets 19. Similarly, the fabric layer 176 of the gusset-flaps can be composed of any of the materials suitable for forming the fabric layer 136 of the leg gussets. In the shown arrangements, the barrier layer and fabric layer are substantially coextensive, but may optionally be non-coextensive. Desirably, the fabric layer 176 is arranged for placement against the wearer's skin, although the barrier layer 174 may optionally be appointed for placement immediately adjacent the wearer's skin.

In particular arrangements of the invention, each containment flap section 144 includes at least one of the elastomeric members 68 attached to the containment flap section 144 at a location which is proximate the movable edge portion 66 of the containment flap section, and includes at least one base elastomeric member 68b attached to the containment flap section at a location which is intermediate the movable edge portion 66 and the fixed edge 64, and has a spacing distance 166 which is not more than about 8 mm from the fixed edge 64 of the containment flap section 144. In desired arrangements, the base elastomeric member can be attached between the movable edge portion 66 and the fixed edge 64, and located substantially immediately adjacent to the fixed edge 64 of the containment flap section 144.

As representatively shown, the article of the invention can be configured with each gusset-flap 140 connected directly or indirectly to an inwardly facing, appointed bodyside surface of the topsheet layer 28. Each gusset-flap member 140 can have a length 168 thereof which extends along at least about 20 percent of the total longitudinal length 180 (FIG. 7) of the article. In other configurations, each gusset-flap member 140 can extend along at least about 30 percent, and alternatively at least about 40 percent of the longitudinal length 180 of the article to provide improved effectiveness. If desired, each gusset-flap member can extend along a length 168 which can be up to 100 percent of the total longitudinal length of the article to provide further gasketing and containment.

Alternatively, each gusset-flap member can extend along a length which is not more than about 80 percent, and optionally is not more than about 70 percent of the total longitudinal length of the article to provide desired performance.

Each gusset section 142 of the gusset-flap 140 can be in a bridging configuration across its associated, concave side edge contour 15 of the backsheet layer along a length 182 which is at least about 20 percent of the longitudinal length 180 of the article. In other configurations, each gusset section can be in a bridging configuration across its associated, concave side edge contour 15 of the backsheet layer along a length 182 which is at least about 30 percent, and alternatively is at least about 40 percent of the extent of the longitudinal length 180 of the article to provide improved effectiveness. If desired, each leg gusset section 142 can be in a bridging configuration along a length which can be up to 100 percent of the total longitudinal length of the article to provide further gasketing and containment. Alternatively, each gusset section can be in a bridging configuration along a length which is not more than about 80 percent, and optionally is not more than about 70 percent of the total longitudinal length of the article to provide desired performance and cost effectiveness.

In particular aspects of the invention, the gusset-flap members 140 are configured to substantially avoid intersecting the locations of the waist pocket members 80. Accordingly, each of the gusset-flap members can be constructed to terminate at positions which are spaced away from the terminal edges of the pocket sections 84 of the waist pocket members.

It should be readily appreciated that the gusset section 142 of the gusset-flap member 140 can incorporate the various structures described with respect to the leg gusset member 19. In addition, it should be readily appreciated that the containment flap section 144 of the gusset-flap member 140 can incorporate the various configurations and structures described with respect to the containment flaps 62.

As previously described in the context of other components of the article, each gusset-flap 140 may have an overall longitudinal length which is substantially equal to the overall, total length of the article. Alternatively, each gusset-flap may have a length which is less than the overall, total length of the article, and the relatively shorter gusset-flap may be configured with a zoned-placement at a selected location along an appointed portion of the overall length of the article. Optionally, each gusset-flap 140 may have a total length which is substantially equal to or less than the overall, total length of the absorbent body structure 32, and the relatively shorter containment flap may be configured with a zoned-placement at a selected location along an appointed portion of the overall length of the absorbent body structure.

To further control the operation of the gusset-flap structure, desirably the containment flap section 144, the flap elastic members may be uniformly spaced across the entire width of the lamina (as determined along a dimension which is substantially perpendicular to the stretching dimension of the elastic member), or they may be grouped into discrete and distinct functional sets. Similar to the configurations described for other components of the article, such as the component sections of the waist pocket member 80, the multiple grouping of elastics may be placed in either or both of the gusset or containment flap sections of the gusset-flap member 80 to control the operation of the gusset-flap and enhance its performance.

In further aspects of the invention, the elastic members in either the gusset section 142, the containment flap section 144 or both sections may be operably zone-tensioned in configurations similar to those described for other components of the article, such as the waist pocket member 80 or the containment flaps 62. Desirably, the zone tensioning is configured to substantially limit the elasticized gathering to a medial, longitudinally-central section of the gusset-flap member. The zone tensioning may be achieved in a variety of ways. For example, an adhesive or other bonding mechanism may be applied only in the areas where the retraction of the elastic members is intended to gather the flap composite. In the regions where the bonds are absent, the remaining elastic members can contract substantially without gathering the flap composite. Alternatively, other techniques, such as ultrasonics, can be employed to operably deaden the elastic members in the regions where elastic retraction is not desired.

With reference to FIGS. 11 and 12, particular aspects of the invention can be configured with the gusset-flap member 144 secured to the article with a generally H-shaped pattern of attachment 154. The H-attachment includes a longitudinally extending crossbar section 156, and substantially laterally extending leg sections composed of segments 160 and 162. The leg segments 160 are constructed to operably secure longitudinal end portions 150 of the gusset section 142 to lie substantially along a plane generally defined by the side margins of the backsheet layer 30. In addition, attachment leg segments 162 operably secure longitudinal end portions 152 of the containment flap section 144 to lie substantially along a plane generally defined by the topsheet layer 28. In particular aspects of the invention, the cross bar section of each H-shaped attachment is located laterally outboard of the absorbent body structure 32, at least within the crotch portion 18 of the article. Accordingly, the location of the longitudinal, cross bar section of the H-shaped attachment is laterally outboard of the retention portion 48 in at least the crotch portion of the article. Additionally, the location of the longitudinal, cross bar section of the attachment can be laterally outboard of the wrapsheet 70 in at least the crotch portion of the article.

In the various arrangements of the invention, the selected absorbent body, such as provided by the absorbent body structure 32, is positioned and operably secured between the topsheet 28 and the backsheet 30 to form the diaper 10. The absorbent body has a construction which is generally compressible, conformable, non-irritating to the wearer's skin, and capable of absorbing and retaining liquid body exudates. It should be understood that, for purposes of this invention, the absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Preferably, each piece is connected to an adjacent portion of the absorbent structure by a suitable bonding and/or fiber entanglement mechanism, such as ultrasonic or adhesive bonding, or mechanical or hydraulic needling.

In the representatively shown embodiments, absorbent structure 32 has a liquid-acquisition zone, a target zone, and a contoured, curvilinear periphery, particularly along its side edges. The two generally mirror-image, inwardly bowed, lateral edges provide for a narrower intermediate section suitable for positioning in the crotch of the wearer. In the shown absorbent structure 32, a front section thereof includes two transversely spaced ear regions and a central region. The target zone encompasses the area where repeated liquid surges typically occur in absorbent structure 32. When the diaper is worn, the ear regions are configured to generally engage the sides of the wearer's waist and torso, and central region is configured to generally engage the medial portion of the wearer's waist and torso.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied. In a particular aspect of the invention, the absorbent structure has an absorbent capacity of at least about 300 gm of synthetic urine. Alternatively, the absorbent structure can have an absorbent capacity of at least about 400 gm of synthetic urine to provide improved performance.

Various types of wettable, hydrophilic fibrous material can be used to form the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for the surge management portion 46 can be provided by a CAHN, SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

Retention portion 48 can comprise a matrix of hydrophilic fibers, such as a web of cellulosic fluff, mixed with particles of high-absorbency material. In particular arrangements, retention portion 48 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent structure and relatively higher concentrations toward the outside of the absorbent structure. Suitable z-gradient configurations are described in U.S. Pat. No. 4,699,823 issued Oct. 13, 1987 to Kellenberger et al., the disclosure of which is incorporated herein by reference in a manner that is consistent with the present description. The superabsorbent particles may also be arranged in a generally discrete layer within the matrix of hydrophilic fibers or may be configured as discrete, separate pocket regions of superabsorbent material. In addition, two or more different types of superabsorbent may be selectively positioned at different locations within or along the fiber matrix.

The high-absorbency material may comprise absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48.

Preferred for use are particles having an average size of from about 20 microns to about 1 millimeter. "Particle size" as used herein means the weighted average of the smallest dimension of the individual particles.

Suitable high-absorbency materials can have particular characteristics of Absorbent Capacity (sometimes referred to as "AC"), Deformation Under Load (sometimes referred to as "DUL"), and the Wicking Index (sometimes referred to as "WI"). These parameters are described in detail in U.S. patent application Ser. No. 757,787 of S. Byerly et al., entitled ABSORBENT COMPOSITES AND ABSORBENT ARTICLES CONTAINING SAME and filed on Sep. 11, 1991 (Attorney Docket No. 10,174), the disclosure of which is hereby incorporated by reference in a manner that is consistent with the present specification.

In a particular aspect of the invention, absorbent retention portion 48 comprises a matrix of substantially hydrophilic fibers having a quantity of high-absorbency material distributed therein. Selected superabsorbent polymers having improved absorbent properties can be important for maximizing the performance while retaining the desired thinness of the absorbent article. To provide improved performance, the particles of superabsorbent material can be selected to provide an absorbency-under-load (AUL) value which is within the range of about 25–40, and provide a Absorbent Capacity (AC) value which is within the range of about 32–48. The rate of liquid uptake by the superabsorbent material is within the range of about 3–15 g/g (grams liquid per gram superabsorbent) at 30 seconds of absorbency under load, 6.5–21 g/g at 5 minutes absorbency under load and 25–40 g/g at 60 minutes absorbency under load.

A suitable method for determining AUL is described in detail in U.S. Pat. No. 5,147,343 of S. Kellenberger, granted Sep. 15, 1992 and entitled ABSORBENT PRODUCTS CONTAINING HYDROGELS WITH ABILITY TO SWELL AGAINST PRESSURE (Attorney Docket No. 8786.1); and also published Nov. 2, 1989 as European Patent Application No. EP 0 339 461 A1; the disclosure of which is hereby incorporated by reference in a manner that is consistent with the present specification.

An example of superabsorbent polymer suitable for use in the present invention is SANWET IM 3900 polymer available from Hoechst Celanese, a business having offices in Portsmouth, Va. Other suitable superabsorbents may include DOW DRYTECH 2035LD polymer obtained from Dow Chemical Co., a business having offices in Midland, Mich.; or FAVOR SAB 870M polymer available from Stockhausen, Inc., a business having offices in Greensboro, N.C.

The matrix of hydrophilic fibers comprising retention portion 48 may be a layer of cellulosic wood pulp fluff, and the particles of superabsorbent polymer can be distributed within the matrix of hydrophilic fibers. The hydrophilic fibers and high-absorbency particles can be provided in a fiber-to-particle ratio which is not more than about 75:25, alternatively, is not more than about 70:30, and optionally, is not more than about 55:45, by weight. In further aspects of the invention, the fiber-to-particle ratio is not less than about 25:75, preferably is not less than about 30:70 and more preferably is not less than about 45:55, by weight. Such fiber-to-particle ratios can be particularly desirable in the target zone of the absorbent structure. In particular embodiments of the invention, the fiber-to-particle weight ratio is not more than about 65:35 and is not less than about 50:50 to provide desired performance.

The hydrophilic fibers and high-absorbency particles can form an average composite basis weight which is within the range of about 400–900 gsm. Again, such basis weight is particularly desirable in the target zone of the absorbent structure. In certain aspects of the invention, the average composite basis weight is within the range of about 500–800 gsm, and preferably is within the range of about 550–750 gsm to provide desired performance.

To provide the desired thinness dimension to the various configurations of the absorbent article of the invention, retention portion 48 can be configured with a bulk thickness which is not more than about 0.6 cm. Preferably, the bulk thickness is not more than about 0.53 cm, and more preferably is not more than about 0.5 cm to provide improved benefits. The bulk thickness is determined under a restraining pressure of 0.2 psi (1.38 kPa).

The density of retention portion 48 or other component of the absorbent article can be calculated from its basis weight and thickness. With respect to diapers, for example, the weight and thickness are measured on newly unpacked, unfolded and dry diapers at a restraining pressure of 0.2 psi (1.38 kPa). Conventional thickness measuring devices may be employed to determine the thickness needed to calculate the density.

In the illustrated embodiments of the invention, absorbent retention portion 48 includes 4–22 grams of wood pulp fluff, preferably includes about 8–18 grams of fluff and more preferably includes about 12–14 grams of fluff to provide desired benefits. The wood pulp fluff generally provides shape and form to diaper 10, and carries and positions the particles of superabsorbent polymer or other high-absorbency material. Retention portion 48 can contain about 7–12 grams of superabsorbent polymer, and in the shown embodiment, contains about 8 grams of superabsorbent polymer. Sufficient superabsorbent polymer is incorporated into retention portion 48 to provide an adequate total absorbent capacity of at least about 300 gm of synthetic urine. For example, a medium size diaper for an infant weighing about 16–28 lb (about 7–13 kg) can typically have a total retention capacity of about 400 grams of synthetic urine.

The fluff and superabsorbent particles can be selectively placed into desired zones of retention portion 48. For example, the fluff basis weight may vary across the width dimension of retention portion 48. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material may be distributed down a medial region of retention portion 48 which extends along the length dimension of the retention portion and measures about 3.5–4.5 inches (about 8.9–11.4 cm) in width. In addition, the superabsorbent material may have a selected zoned placement to reduce the amount of superabsorbent material located proximate the side and end edges of the retention portion. The reduced amounts of superabsorbent material at the edges of the retention portion can improve the containment of the superabsorbent particles within the fibrous fluff matrix of retention portion 48. The pulsed, zoned placement of the superabsorbent material can, for example, be achieved by the method and apparatus described in U.S. Pat. No. 5,028,224 to C. Pieper et al., entitled METHOD AND APPARATUS FOR INTERMITTENTLY DEPOSITING PARTICULATE MATERIAL IN A SUBSTRATE and issued Jul. 2, 1991 (Attorney Docket No. 8761), the disclosure of which is hereby incorporated by reference in a manner that is consistent herewith.

In a particular aspect of the invention, absorbent structure 32 can be generally T-shaped with the laterally extending cross-bar of the "T" generally corresponding to the front waistband portion of the absorbent article for improved performance, especially for male infants. In the illustrated embodiments, for example, the retention portion across the ear section of the front waistband region of the article has a cross-directional width of about 9.0 inches (about 22.9 cm), the narrowest portion of the crotch section has a width of about 3.5 inches (about 8.9 cm) and the back waistband region has a width of about 4.5 inches (about 11.4 cm).

The entire absorbent structure 32, or any individual portion thereof, such as the retention portion, can be overwrapped in a hydrophilic high wet-strength envelope web, such as a high wet-strength tissue or a synthetic fibrous web. Such overwrapping web can also increase the in-use integrity of the absorbent structure. The web can be suitably bonded, such as with adhesive, to absorbent structure 32 and to other components of the product construction.

Due to the high concentrations of superabsorbent particles, or other high-absorbency material, in retention portion 48, there can be an increased difficulty with regard to containing the high-absorbency particles within the retention portion and restricting the movement or migration of the superabsorbent onto the bodyside of the diaper. To improve the containment of the high-absorbency material, absorbent structure 32 can include an improved overwrap, such as a wrap sheet 70, placed immediately adjacent and around retention portion 48. The wrap sheet is preferably a layer of absorbent material which covers the major bodyside and outerside surfaces of the retention portion, and preferably encloses substantially all of the peripheral edges of the retention portion to form a substantially complete envelope thereabout. Alternatively, the wrap sheet can provide an absorbent wrap which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the retention portion at the waistband regions of the article.

Absorbent wrap 70 may comprise a multi-element wrapsheet which includes a separate bodyside wrap layer and a separate outerside wrap layer, each of which extends past all or some of the peripheral edges of retention portion 48, as representatively shown in FIG. 1. Such a configuration of the wrap sheet can, for example, facilitate the formation of a substantially complete sealing and closure around the peripheral edges of retention portion 48. In the back waistband portion of the illustrated diaper, the absorbent wrap may also be configured to extend an increased distance away from the periphery of the retention portion to add opacity and strength to the back ear sections of the diaper. In the illustrated embodiment, for example, the bodyside and outerside layers of absorbent wrap 70 extend at least about ½ inch (about 1.3 cm) beyond the peripheral edges of the retention portion to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 70 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearers skin, and the high porosity, lower basis weight outerside layer can help reduce costs and facilitate the processibility of the absorbent pad.

To provide the bonding between the bodyside and outerside portions of absorbent wrap 70, an adhesive, such as NATIONAL STARCH 72-3723 adhesive, can be printed onto the appointed bonding areas of the absorbent wrap with, for example, a rotogravure-type system. With alternative arrangements having an absorbent wrap composed of a nonwoven meltblown fibrous web, the peripheral sealing of the bodyside and outerside wrap layers may be accomplished by employing hot calendering to provide a sealed strip region around the periphery of the retention portion.

Due to the thinness of retention portion 48 and the high superabsorbent concentrations within the retention portion, the liquid uptake rates of the retention portion, by itself, may be too low, or may not be adequately sustained over multiple insults of liquid into the absorbent structure. The addition of a porous, liquid-permeable layer of surge management material, however, can advantageously improve the overall uptake rate of the composite absorbent structure. Surge management portion 46 is typically less hydrophilic than retention portion 48, and has an operable level of density and basis weight to quickly collect and temporarily hold liquid surges, to transport the liquid from its initial entrance point and to substantially completely release the liquid to other parts of the absorbent structure 32, particularly retention portion 48. This configuration can help prevent the liquid from pooling and collecting on the portion of the absorbent garment positioned against the wearer's skin, thereby reducing the feeling of wetness by the wearer.

Various woven and nonwoven fabrics can be used to construct surge management portion 46. For example, the surge management portion may be a layer composed of a meltblown or spunbonded web of polyolefin fibers. The surge management layer may also be a bonded-carded-web or an airlaid web composed of natural and synthetic fibers. The bonded-carded-web may, for example, be a powder-bonded-carded web, an infrared bonded carded web, or a through-air-bonded-carded web. The infrared and through-air bonded carded webs can optionally include a mixture of different fibers, and the fiber lengths within a selected fabric web may be within the range of about 1.0–3.0 inch. The surge management portion may be composed of a substantially hydrophobic material, and the hydrophobic material may optionally be treated with a surfactant or otherwise processed to impart a desired level of wettability and hydrophilicity.

The representative diaper 10 can include a surge management portion 46 which is arranged in a direct, contacting liquid communication with an adjacent absorbent retention portion 48. As representatively shown, surge management portion 46 may be configured for placement adjacent an outwardly facing, outerside of topsheet 28. Optionally, the surge management portion can be placed adjacent an inwardly facing, bodyside surface of topsheet layer 28. The shown configuration of the surge management portion is operably connected to the topsheet layer with a conventional pattern of adhesive, such as a swirl adhesive pattern. In addition, the surge management portion can be operably connected to the bodyside layer of wrapsheet 70 with a conventional pattern of adhesive. The amount of adhesive add-on should be sufficient to provide the desired levels of bonding, but should be low enough to avoid excessively restricting the movement of liquid from the topsheet layer, through the surge management portion and through the wrapsheet layer.

The retention portion 48 is positioned in liquid communication with surge management portion 46 to receive liquids released from the surge management portion, and to hold and store the liquid. In the shown embodiments, surge management portion 46 comprises a separate layer which is positioned over another, separate layer comprising the retention portion, thereby forming a dual-layer arrangement. The surge management portion serves to quickly collect and temporarily hold discharged liquids, to transport such liquids from the point of initial contact and spread the liquid to other parts of the surge management portion, and then to substantially completely release such liquids into the layer or layers comprising retention portion 48.

The representatively shown configuration of the surge management portion is substantially free of absorbent gelling material. Surge management portion 46 may, however, contain a very small amount of particulate gelling material to help acquire an initial liquid surge, but the amount should not be excessive. When excessive amounts of particulate absorbent gelling material are maintained in the target zone, however, the particles can cause the structure to retain and hold unacceptably high amounts of the liquid. In addition, the transport of liquids away from the target zone to other sections of absorbent structure 32, particularly retention portion 48, can be undesirably impaired. As mentioned previously, surge layer 46 can be a separately formed layer, which lies adjacent the outwardly facing surface of topsheet 28 between the retention portion and topsheet. Thus, surge management portion 46 need not comprise the entire thickness of absorbent structure 32. The retention portion can optionally include a recess area which wholly or partially surrounds surge management portion 46, or the retention portion can be entirely positioned below the surge management portion. The arrangement which includes the recess in retention portion 48 can advantageously increase the area of contact and liquid communication between the retention portion and surge management portion 48. It should be understood, however, that surge management portion 46 could optionally be constructed to extend through the entire thickness of absorbent structure 32 so that the capillary flow of liquid into retention portion 48 occurs primarily in a generally sideways (X–Y) direction.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized. In certain embodiments, for example, the surge management portion can be generally rectangular-shaped.

In the various configurations of the invention, surge management portion 46 may extend over the complete length of retention portion 48, or may extend over only a part of the retention portion length. Where the surge management portion extends only partially along the length of the retention portion, the surge management portion may be selectively positioned anywhere along absorbent structure 32. For example, surge management portion 46 may function more efficiently when it is offset toward the front waistband of the garment and transversely centered within a front section of absorbent structure 32. Thus, surge management portion 46 can be approximately centered about the longitudinal center line of absorbent structure 32, and positioned primarily in a central region of a front section of the absorbent structure 32.

In other aspects of the invention, the end edges of the surge management portion can be spaced longitudinally inboard from the end edges of the retention portion 48. In particular configurations of the invention, the corresponding, relatively adjacent front end edge of surge management portion 46 can be spaced a predetermined discrete distance from a front waistband end edge of the retention portion 48.

It has been found that an effective fabric for constructing the surge management portion can be distinctively characterized by particular parameters. Such parameters include, for example, basis weight, permeability, porosity, surface area per void volume (SA/VV), compression resiliency and saturation capacity. Further parameters can include a bonding matrix which will help stabilize the pore size structure, and hydrophilicity. The bond-matrix and the blend of fiber deniers can advantageously provide for and substantially maintain a desired pore size structure.

Additional details regarding the surge materials and suitable techniques for determining the above-described parameters are set forth in U.S. patent application Ser. No. 206,986 of C. Ellis and D. Bishop, entitled, FIBROUS NONWOVEN WEB SURGE LAYER FOR PERSONAL CARE ABSORBENT ARTICLES AND THE LIKE, and filed Mar. 4, 1994 (attorney docket No. 11,256); and U.S. patent application Ser. No. 206,069 of C. Ellis and R. Everett, entitled, IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387); the disclosures of which are hereby incorporated by reference in a manner that is consistent herewith.

In desired configurations of the invention, the surge material can include natural fibers, synthetic fibers, such as synthetic polymer fibers, and combinations thereof. The fabric can, for example, be composed of polyolefin fibers, and in particular configurations the fibers can include bicomponent fibers. For example, polypropylene/polyethylene bicomponent fibers may be employed to form the bicomponent fiber portion of any of the described fabrics. In addition, the bicomponent fibers may be flat crimped or helically crimped.

In the shown configuration of the article, the side panel members 56 are separately provided members which are operably connected and attached to laterally opposed end sections of the back waistband portion of backsheet 30. In particular, each side panel is affixed to extend away from a corresponding terminal edge of the backsheet layer. The side panels can be composed of a substantially non-elastomeric material, such as polymer films, woven fabrics, nonwoven fabrics or the like, as well as combinations thereof. In particular aspects of the invention, the side panels are composed of an elasticized material, such as a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. 4,663,220 issued May 5, 1987 to T. Wisneski et al., the disclosure of which is hereby incorporated by reference. Examples of composite fabrics comprising at least one layer of nonwoven textile fabric secured to a fibrous elastic layer are described in European Patent Application No. EP 0 110 010 published on Apr. 8, 1987 as EP 0 217 032 A2 with the inventors listed as J. Taylor et al., the disclosure of which is hereby incorporated by reference. Examples of NBL materials are described in U.S. Pat. No. 5,226,992 issued Jul. 13, 1993 to M. Mormon, the disclosure of which is hereby incorporated by reference.

Examples of articles which include elasticized side panels and selectively configured fastener tabs are described in U.S. patent application Ser. No. 168,615 of T. Roessler et al., entitled DYNAMIC FITTING DIAPER, and filed Dec. 16, 1993 (Attorney docket No. 10,961). Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995 (Attorney docket No. 11,186); in U.S. patent application Ser. No. 286,086 of D. Fries, entitled A PROCESS FOR ASSEMBLING ELASTICIZED EAR PORTIONS and filed Aug. 3, 1994 (Attorney docket No. 11,169); in U.S. patent application Ser. No. 08/415,383 of D. Fries, entitled AN ASSEMBLY PROCESS FOR A LAMINATED TAPE and filed Apr. 3, 1995 (attorney docket No. 11,950), and in U.S. patent application Ser. No. 08/415,382 of D. Fries, entitled AN ABSORBENT ARTICLE WITH A LAMINATED TAPE and filed Apr. 3,1995 (attorney docket No. 11,990). The entireties of the disclosures of the above-described documents are incorporated herein by reference in a manner that is consistent (not in conflict) herewith.

The fastener system can include a separately provided reinforcement strip 88 which is composed of a strengthening and/or stiffening material, and is laminated to an appointed first surface of each of the side panel members 56 at the outboard region of the side panel. The shown reinforcement strip extends along substantially the entire length of the outboard end portion of the panel member 56. In addition, the reinforcement strip has a length which is greater than the length dimension of the securing means 44 on the user-bond portion 38 of the fastener tab 36. The reinforcement strip 88 can, for example, be composed of a release tape, and the release tape can include a substrate composed of a polymer film, such as a polypropylene film. Suitable release tape materials are available from Avery Corp., a business having offices located in Painesville, Ohio.

The release tape configuration of the reinforcement strip 88 can have an appointed release surface and an oppositely located attachment surface. A suitable release material, which has a limited low level adhesion to conventional pressure-sensitive adhesives, is positioned and distributed over the release surface, and a suitable attachment mechanism, such as a layer of construction adhesive, is distributed over the attachment surface. The construction adhesive is employed to affix the reinforcement strip 88 onto an appointed section of the final article. In particular, the strip of release tape can be operably bonded and laminated to the outboard region of the panel member 56 along the first surface of the panel member. The shown strip of release tape can be configured with its terminal outboard edge positioned substantially coterminous and substantially coextensive with the outboard edge of the panel member 56. In addition, the width of the release tape along the cross-direction 24 is desirably equal to or greater than the width of the securing means 44 provided on the user-bond region 38 of the fastener tab 36.

The illustrated fastening system includes a complementary, opposed pair of fastener tabs 36, which provide a mechanism for holding the article on the wearer. Each of the fastener tabs includes a tab substrate 86, which may be composed of various substrate materials. For example, the shown embodiment of the tab substrate can be composed of a polymer film, such as a polypropylene film. Suitable film materials are available from Avery Corp., a business having offices located in Painesville, Ohio. Alternatively, the securement web may include a woven or nonwoven fabric, such as spunbond nonwoven fabric.

The representatively shown tab substrate 86 includes an appointed securement surface and an opposed user surface, and includes a selected securing means which is positioned onto the securement surface of the tab substrate. The securing means may be provided by an adhesive, a cohesive material, a cooperating component of a interengaging, mechanical fastener, snaps, pins or buckles and the like, as well as combinations thereof. For example, the securing means may include a hook (e.g. mushroom-head) component or a loop component of a hook-and-loop fastener. In the shown configuration, the securing means is provided by a layer of primary adhesive distributed over the appointed securing surface, and the fastening system provides an adhesive fastener tab. The fastener tabs can be constructed to releasably adhere to an appointed landing zone patch 92 which is attached to the front waistband section of the diaper to provide a refastenable adhesive fastening system.

With the adhesive securing means, the layer of primary adhesive can be employed to operably laminate and affix the appointed factory-bond region 39 of the fastener tab 36 to the outboard region of the panel member 56 along an appointed second surface of the panel member. Other types of connecting means, such as thermal bonds, sonic bonds, mechanical stitching, stapling and the like, as well as combinations thereof, may alternatively be employed to permanently attach the fastener tab to the panel member. For example, ultrasonic bonds may be employed to provide a selected supplemental bonding.

With reference to FIG. 1, the fastener tab 36 includes a factory-bond section 39 which overlaps the outboard edge of the panel member 56, and extends beyond the panel member to provide the user-bond region of the fastener tab. In particular arrangements of the invention, the fastener tab can have a relatively wide user-bond section in combination with a relatively narrower intermediate section. The intermediate section is positioned between the user-bond and factory-bond sections of the fastener tab. In a further aspect of the invention, the fastener tab 36 may optionally include a finger tab region. The finger tab can be substantially non-securing, and can provide an area that can be readily grasped by the user without contaminating or otherwise adversely affecting the securing means.

Various types and arrangements of interengaging mechanical securing means can be employed to provide an operable fastening system for the various configurations of the invention. Representative examples of suitable mechanical fastener configurations are described in U.S. patent application Ser. No. 366,080 by G. Zehner et al., filed Dec. 28, 1994 and entitled HIGH-PEEL TAB FASTENER (attorney docket No. 11,571), and in U.S. patent application Ser. No. 421,640 by P. VanGompel et al., entitled MULTI-ATTACHMENT FASTENING SYSTEM and filed Apr. 13, 1995 (attorney docket No. 11,430), the entire disclosures of which are hereby incorporated by reference in a manner that is consistent herewith.

The following Examples are presented to provide a more detailed understanding of the invention. The Examples are intended to be representative, and are not intended to specifically limit the scope of the invention.

EXAMPLES

Example 1

Each sample was composed of a 1.0 mil (0.0254 mm) thick polyurethane film, grade MP 1882 P, available from JPS Elastomerics Corp., a business having offices in Northampton, Mass. The elastomeric film exhibited inadequate, low stiffness values, which were lower than the testing scale of the test instrument.

Example 2

The samples were taken from PAMPERS Stretch diapers which were distributed by the Procter & Gamble Co., a business having offices in Cincinnati, Ohio. The diapers included a waist flap, and test samples of the waist flaps were taken for testing. The size of each waist flap was too small to test as an individual piece of material. As a result, each test sample included the waist flap material attached to connected sections of the diaper liner sheet and the diaper back sheet. The attachment of the added layers of the liner and backsheet materials is believed to have increased the overall stiffness of each test sample. As a result, it is believed that the observed stiffness values were higher than the values that would have been measured if the tests had been conducted on samples composed of the waist flap material alone. The waist flap in each of the samples in this Example 2 was composed of an elastomeric, three-layer laminate. The laminate was composed of one layer of film (polyethylene:polyvinyl acetate copolymer with $TiO_2$ filler) sandwiched between two layers of polypropylene nonwoven, and was thermally bonded together. The samples exhibited stiffness values that were excessively low.

Example 3

The samples were taken from diapers distributed by Molnlycke A. G., a business having offices in Goteborg, Sweden. The diapers included an inner, body-contacting layer having a relatively large, elongate central opening or aperture therethrough. Longitudinally extending elastics were attached to gather the edge regions of the inner layer which were adjacent the side edges of the aperture. The material of the inner layer located adjacent the longitudinally opposed end edges of the aperture were observed to provide structures which resembled a pair of waist flaps. The Molnlycke diapers provided sufficient material to remove individual samples large enough for stiffness testing. The samples could be taken as if they were removed from raw material stock, and measured 1 inch (2.54 cm) in length by ½ inch (1. 27 cm) in width. Each sample was a nonwoven fabric composed of a polypropylene, bonded-carded web. The samples exhibited stiffness values that were excessively low.

Example 4

Each sample was a laminate composed of a 0.00035 inch (about 0.0089 mm) thick polyethylene film, code SF20 available from Consolidated Thermoplastics Co., a business having offices in Chippewa Falls, Wis. The laminate had 12 strands of LYCRA 470 dtex (decitex) elastomer applied stretched at approximately a 260% elongation, with 5 strands within the pocket section 84 and 7 strands within the flange section 82. The film and elastic strands were assembled and attached to a bicomponent polypropylene/polyethylene fiber spunbond web having 0.6 oz/yd$^2$ (about 20.4 g/m$^2$) basis weight with 6.5 g/m$^2$ of FINDLEY H2096 adhesive employing a meltspray applicator available from J. & M. Laboratories Inc., a business having offices in Dawsonville, Ga. The samples were representative of waist pocket members suitable for the present invention.

Example 5

Each sample was a laminate composed of a 0.00035 inch (about 0.0089 mm) thick polyethylene film, code SF20 available from Consolidated Thermoplastics Co. The laminate had 12 strands of LYCRA 470 dtex elastomer applied at approximately 260% elongation, with 7 strands within the pocket section and with 5 strands within the flange section. The film and elastic strands were glued to a bicomponent polypropylene/polyethylene fiber spunbond fabric having a 0.6 oz/yd$^2$ (about 20.4 g/m$^2$) basis weight, with 6.5 g/m$^2$ of FINDLEY H2096 adhesive using a meltspray applicator available from J. & M. Laboratories Inc. The samples were representative of waist pocket members suitable for the present invention.

Example 6

Each sample was a laminate composed of a 0.0006 inch (about 0.015 mm) thick polyethylene film, code XEM400.1 available from Consolidated Thermoplastics Co. The laminate had 6 strands of GLOSPAN S7 360 denier, with 2 strands within the pocket section applied at approximately 175% elongation and with 4 strands within the flange section applied at approximately 150% elongation. The film and elastic strands were glued to a bicomponent polypropylene/polyethylene fiber spunbond fabric web having 0.6 oz/yd$^2$ (about 20.4 g/m$^2$) basis weight with 5 g/m$^2$ of FINDLEY H9214 adhesive using a swirl applicator. The samples were representative of waist pocket members suitable for the present invention.

Example 7

Each sample was a laminate composed of a 0.0006 inch (about 0.015 mm) thick polyethylene film, code XEM400.1 available from Consolidated Thermoplastics Co. The laminate had 6 strands of GLOSPAN S7 360 denier, with 2 strands within the pocket section applied at approximately 175% elongation and with 4 strands within the flange section applied at approximately 150% elongation. The film and elastic strands were glued to a polypropylene spunbond fabric web having 0.6 oz/yd$^2$ (about 20.4 g/m$^2$) basis weight, with 5 g/m$^2$ of FINDLEY H9214 adhesive using a swirl applicator. The samples were representative of waist pocket members suitable for the present invention.

Example 8

Each sample was a laminate composed of a 0.00035 inch (about 0.0089 mm) thick polypropylene film, code XSF184 available from Consolidated Thermoplastics Co. The laminate had 6 strands of GLOSPAN S7 490 denier, with 2 strands within the pocket section applied at approximately 200% elongation and with 4 strands within the flange section applied at 150% elongation. The film and elastic strands were glued to a bicomponent polypropylene/polyethylene fiber spunbond fibrous web having 0.6 oz/yd$^2$ (about 20.4 g/m$^2$) basis weight with FINDLEY H2096 adhesive using a strand-coating technique. The samples were representative of waist pocket members suitable for the present invention.

The Gurley stiffness values for Examples 1–8 are summarized in the following TABLE 1.

During testing, the room was at standard conditions of 73° F. (about 23° C.) and 50% relative humidity. A suitable device for taking the measurements is a Gurley Digital Stiffness tester, Model 4171-D, available from Teledyne Gurley, a business having offices in Troy, N.Y.; or an equivalent device. The testing procedure was in accordance with TAPPI T543 om-94. Examples 1, and 4 through 8 had the Gurley stiffness values obtained from samples taken from raw material supplies of the described films or laminas.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An absorbent article having a longitudinal length dimension, a lateral cross dimension, a front waistband portion, a back waistband portion, and an intermediate portion which interconnects said front and back waistband portions, said article comprising:

a backsheet layer having a pair of laterally opposed and longitudinally extending side margins, each side margin having an outwardly concave, terminal side edge contour located at appointed leg opening regions in an intermediate portion of each of said side margins, each concave side edge contour having a selected longitudinal extent along said length dimension of said article;

a liquid permeable topsheet layer connected in a superposed facing relation to said backsheet layer;

an absorbent body sandwiched between said topsheet layer and said backsheet layer; and a pair of separately provided gusset-flap members connected to at least one of said backsheet and topsheet layers along each of said appointed leg opening regions, said gusset-flap members including a leg gusset section and a containment flap section, wherein each leg gusset section is configured to extend beyond and bridge across its associated, outwardly concave terminal side edge contour of said backsheet layer, and to provide an elasticized and gathered side margin of said article,

TABLE 1

GURLEY STIFFNESS VALUES
Gurley Stiffness Values (Standard Gurley Units - milligrams force)

| | | | | Example | | | | |
|---|---|---|---|---|---|---|---|---|
| Sample | 1 Film Polyurethane | 2 P & G (waist dam) | 3 Molnlycke (waist dam) | 4 12 Strand 5 Strands in pocket section | 5 12 Strand 7 Strands in pocket section | 6 6 Strand 2 Strands in pocket section | 7 6 Strand 2 Strands in pocket section | 8 6 Strand 2 Strands in pocket section |
| 1 | — | 2.22 | 1.95 | 61.05 | 49.95 | 44.40 | 82.14 | 25.53 |
| 2 | — | 2.78 | 0.83 | 56.61 | 46.62 | 46.62 | 57.72 | 55.50 |
| 3 | — | 3.61 | 0.56 | 75.48 | 48.84 | 57.72 | 55.50 | 26.64 |
| 4 | — | 3.06 | 0.83 | 62.16 | 51.06 | 88.80 | 66.60 | 18.87 |
| 5 | — | 1.95 | 0.83 | 82.14 | 42.18 | 44.40 | 95.46 | 38.85 |
| 6 | — | 2.78 | 0.83 | 83.25 | 58.83 | 77.70 | 117.66 | 39.98 |
| 7 | — | 0.56 | 1.67 | 74.37 | 45.51 | 53.28 | 91.02 | 51.06 |
| 8 | — | 1.95 | 0.56 | 75.48 | 48.84 | 51.06 | 86.58 | 31.08 |
| 9 | — | 3.61 | 1.11 | 63.27 | 51.06 | — | 93.24 | — |
| Ave. | 0.00 | 2.50 | 1.02 | 71.60 | 49.21 | 58.00 | 82.88 | 35.94 |

Ave. = Average
Units of measurement: Standard Gurley Units, which are equivalent to milligrams of force (mf)

each containment flap section is integrally formed with a one of said leg gusset sections to provide a gusset-flap composite with each containment flap section having a substantially fixed edge located proximally adjacent to a one of said elasticized side margins, and having an elasticized and gathered, distal, movable edge portion, each gusset-flap member includes a substantially liquid impermeable barrier layer, a nonwoven fabric layer which is substantially coextensive with said barrier layer and is connected in facing relation with said barrier layer, a plurality of separate, longitudinally extending elastomeric members sandwiched between said barrier layer and said fabric layer within each leg gusset section and a plurality of separate, longitudinally extending elastomeric members sandwiched between said barrier layer and said fabric layer within each containment flap section to provide an elastomeric, gusset-flap composite which is substantially longitudinally gathered, each of said elastomeric members in said containment flap section being attached to at least one of said barrier and fabric layers of the gusset-flap, and wherein each containment flap section has a composite stiffness which is not less than about 5 mg and not more than about 250 mg.

2. An absorbent article having a longitudinal length dimension, a lateral cross dimension, a front waistband portion, a back waistband portion, and an intermediate portion which interconnects said front and back waistband portions, said article comprising:

a backsheet layer having a pair of laterally opposed and longitudinally extending side margins, each side margin having an outwardly concave, terminal side edge contour located at appointed leg opening regions in an intermediate portion of each of said side margins, each concave side edge contour having a selected longitudinal extent along said length dimension of said article;

a liquid permeable topsheet layer connected in a superposed facing relation to said backsheet layer;

an absorbent body sandwiched between said topsheet layer and said backsheet layer; and a pair of separately provided gusset-flap members connected to at least one of said backsheet and topsheet layers along each of said appointed leg opening regions, said gusset-flap member including a leg gusset section and a containment flap section, wherein each leg gusset section is configured to extend beyond and bridge across its associated, outwardly concave terminal side edge contour of said backsheet layer, and to provide an elasticized and gathered side margin of said article, each containment flap section is integrally formed with a one of said leg gusset sections to provide a gusset-flap composite with each containment flap section having a substantially fixed edge located proximally adjacent to a one of said elasticized side margins, and having an elasticized and gathered, distal, movable edge portion, each gusset-flap member includes a substantially liquid impermeable barrier layer, a nonwoven fabric layer which is substantially coextensive with said barrier layer and is connected in facing relation with said barrier layer, a plurality of separate, longitudinally extending elastomeric members sandwiched between said barrier layer and said fabric layer within each leg gusset section and a plurality of separate, longitudinally extending elastomeric members sandwiched between said barrier layer and said fabric layer within each containment flap section to provide an elastomeric, gusset-flap composite which is substantially longitudinally gathered, each of said elastomeric members in said containment flap section being attached to at least one of said barrier and fabric layers of the gusset-flap with an individual, longitudinally extending strip of adhesive, each individual adhesive strip spatially separated from immediately adjacent adhesive strips by a discrete distance, and each individual adhesive strip arranged to attach substantially an individual one of said elastomeric members in said containment flap section to at least one of said barrier and fabric layers of the gusset-flap, and wherein each containment flap section has a composite stiffness which is not less than about 5 mg and not more than about 250 mg.

3. An article as recited in claim 1, wherein said each containment flap section has a composite stiffness which is not less than about 10 mg.

4. An article as recited in claim 1, wherein said each containment flap section has a composite stiffness which is not less than about 15 mg.

5. An article as recited in claim 1, wherein each containment flap section includes at least one of said elastomeric members attached to said containment flap section at a location which is proximate said movable edge portion of said containment flap section; and includes at least one base elastomeric member attached to said containment flap section at a location which is intermediate said movable edge portion and said fixed edge, and is not more than about 8 mm from said fixed edge of said containment flap section.

6. An article as recited in claim 5, wherein said at least one base elastomeric member is attached substantially immediately adjacent to said fixed edge of said containment flap section.

7. An article as recited in claim 1 wherein each said gusset-flap member is secured to said article with a generally H-shaped line of attachment, which secures longitudinal end portions of said gusset section to lie substantially along a plane of said backsheet layer and secures longitudinal end portions of said flap section to lie substantially along a plane of said topsheet layer.

8. An article as recited in claim 1, further comprising an elasticized, waist pocket member connected to at least one of said backsheet and topsheet layers along at least one end margin of said article, said waist pocket member including an extending flange section and an extending pocket section;

said pocket section of said waist pocket member having a substantially fixed edge portion secured to said article, and an elasticized, gathered movable edge portion, and said pocket section including, a substantially liquid impermeable pocket barrier layer, a pocket fabric layer connected in facing relation with said pocket barrier layer, and a plurality of separate, laterally extending pocket elastic members sandwiched between said pocket barrier layer and said pocket fabric layer to provide an elasticized waist pocket composite which is substantially laterally gathered, said pocket section having a stiffness which is at least about 5 mg and is not more than about 250, as determined about a bending axis aligned substantially parallel to said cross-direction of the article.

9. An article as recited in claim 8, wherein said flange section of said waist pocket member includes a substantially liquid impermeable flange barrier layer;

a flange fabric layer connected in facing relation with said flange barrier layer; and a plurality of separate, laterally extending flange elastic members sandwiched between said flange barrier layer and said flange fabric layer to provide an elasticized flange composite which is substantially laterally gathered by said flange elastic members.

10. An article as recited in claim 9, wherein said pocket section of said waist pocket member is integrally formed with said flange section of said waist pocket member; said pocket barrier layer is integrally formed with said flange barrier layer to provide a flange-pocket barrier layer; and said fabric pocket layer is integrally formed with said fabric flange layer to provide a flange-pocket fabric layer.

11. An article as recited in claim 10, wherein said flange-pocket barrier layer is substantially coextensive with said flange-pocket fabric layer.

12. An article as recited in claim 9, wherein said elastic members in said flange section are spaced from said elastic members in said pocket section by a boundary space which provides a separation distance of at least about 2 mm.

13. An article as recited in claim 12, wherein at least one of said elastic members in said pocket section is located between said substantially fixed edge portion and said movable edge portion of said pocket section, and is spaced from said substantially fixed edge portion of said pocket section by a proximal spacing distance of not more than about 20 mm.

14. An article as recited in claim 10, wherein said pocket section of said waist pocket member is secured to said topsheet by a region of attachment which is substantially restricted to said boundary space in at least a section of said boundary space which is in a laterally medial portion of said article.

15. An article as recited in claim 10, wherein said pocket section of said waist pocket member has laterally opposed end sections which are secured to said topsheet to lie substantially flat against said topsheet.

16. An article as recited in claim 12, further including fastener tabs attached at laterally opposed sides of the article, said fastener tabs substantially aligned along a central, cross-directional alignment line which substantially coincides with, and lies within, said boundary space which separates said set of elastic members in said pocket member pocket section from said set of elastic members in said pocket member flange section.

17. An article as recited in claim 8, further including fastener tabs attached at laterally opposed sides of the article, wherein a distal, terminal edge of said pocket section of the pocket member is approximately aligned with a central force line which is created when a tensioning force is applied to the fastening tabs.

18. An article as recited in claim 8, wherein each said leg gusset extends along a longitudinal length which is not more than about 80 percent of a total longitudinal length of said article, and substantially avoids intersecting with said pocket member.

\* \* \* \* \*